United States Patent [19]
Uchino et al.

[11] Patent Number: 6,001,068
[45] Date of Patent: Dec. 14, 1999

[54] GUIDE WIRE HAVING TUBULAR CONNECTOR WITH HELICAL SLITS

[75] Inventors: Syunichi Uchino; Kenichi Yasuda, both of Shizuoka-ken, Japan

[73] Assignee: Terumo Kabushiki Kaisha, Tokyo, Japan

[21] Appl. No.: 08/967,328

[22] Filed: Oct. 21, 1997

[30] Foreign Application Priority Data

Oct. 22, 1996 [JP] Japan ..................................... 8-298179
Aug. 11, 1997 [JP] Japan ..................................... 9-230346

[51] Int. Cl.⁶ ......................................................... A61B 5/00
[52] U.S. Cl. ............................................ 600/585; 600/434
[58] Field of Search ................................. 600/434, 435, 600/433, 585

[56] References Cited

U.S. PATENT DOCUMENTS

| | | | |
|---|---|---|---|
| 4,875,489 | 10/1989 | Messner et al. | 600/585 |
| 5,213,111 | 5/1993 | Cook et al. | 600/585 |
| 5,242,759 | 9/1993 | Hall | 428/610 |
| 5,341,818 | 8/1994 | Abrams et al. | 600/585 |
| 5,365,943 | 11/1994 | Jansen | 600/585 |
| 5,409,015 | 4/1995 | Palermo | 600/585 |
| 5,415,178 | 5/1995 | Hsi et al. | 600/585 |
| 5,546,958 | 8/1996 | Thorud et al. | 600/585 |
| 5,569,200 | 10/1996 | Umeno et al. | 604/96 |
| 5,573,520 | 11/1996 | Schwartz et al. | 600/585 |
| 5,636,641 | 6/1997 | Fariabi | 600/585 |
| 5,636,642 | 6/1997 | Palermo | 600/585 |
| 5,637,089 | 6/1997 | Abrams | 600/585 |
| 5,788,653 | 8/1998 | Lorenzo | 600/585 |

FOREIGN PATENT DOCUMENTS

| | | |
|---|---|---|
| 0 340 304 | 7/1988 | European Pat. Off. . |
| 0 377 453 | 1/1990 | European Pat. Off. . |
| 0 744 186 | 11/1996 | European Pat. Off. . |
| 03031472 | 7/1991 | Japan . |
| 3-122850 | 12/1991 | Japan . |
| 04009162 | 1/1992 | Japan . |
| 06319803 | 11/1994 | Japan . |
| 08243168 | 9/1996 | Japan . |
| 09084871 | 3/1997 | Japan . |
| 91/00051 | 1/1991 | WIPO . |
| 94/20015 | 9/1994 | WIPO . |
| 94/20165 | 9/1994 | WIPO . |

*Primary Examiner*—Cary O'Connor
*Assistant Examiner*—Charles Marmor, II
*Attorney, Agent, or Firm*—Burns, Doane, Swecker & Mathis, LLP

[57] ABSTRACT

A guide wire includes a first wire located at the distal end of the guide wire, a second wire located at the proximal end of the guide wire and having a flexural rigidity greater than that of the first wire, and a tubular connector for joining the first and second wires. The connector has one or more grooves or slits formed on the distal side of the boundary between the first wire and the second wire. The connector is formed of a material different from the material of the first wire. The proximal portion of the first wire is provided with a thin metal coating. The first wire is joined to the connector by brazing at the portion provided with the thin metal coating.

22 Claims, 17 Drawing Sheets

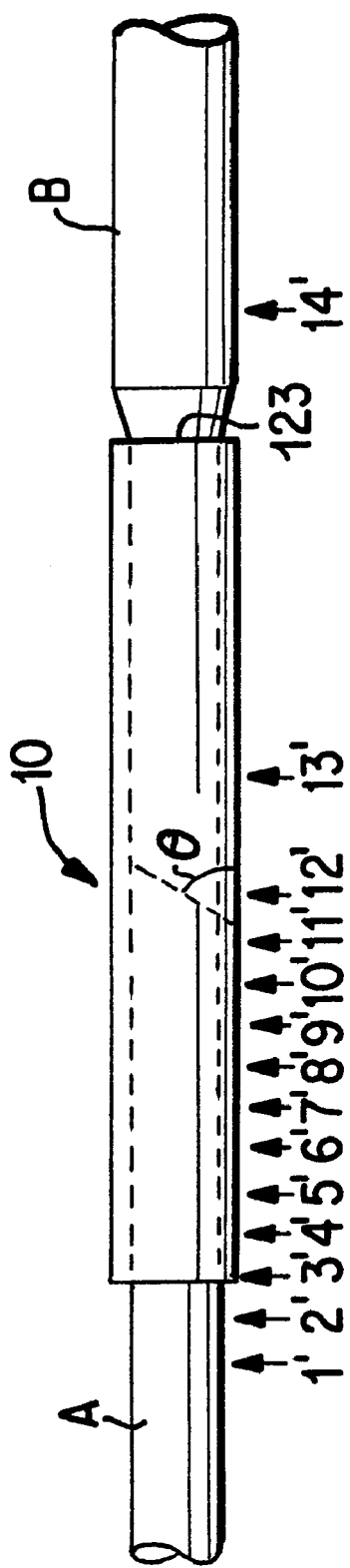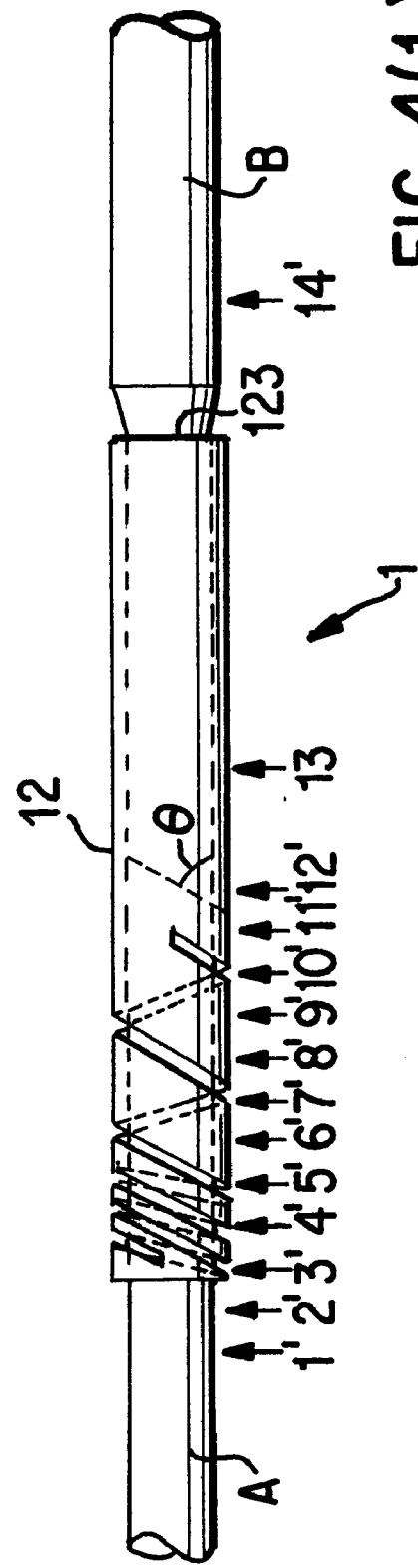

GUIDE WIRE HAVING TUBULAR CONNECTOR WITH HELICAL SLITS

BACKGROUND OF THE INVENTION

This invention relates to a guide wire, especially a guide wire used to guide a catheter or other tubular medical devices to a target place in the body of a patient.

A guide wire is used to guide a catheter in treatment of the body parts on which open surgery is difficult or in treatment or examination for the purpose of reducing the invasiveness to the body such as PTCA (Percutaneous Transluminal Coronary Angioplasty) and cardiovascular angioplasty to the target place in the body. The guide wire used in the PTCA procedure is passed through the catheter before the catheter is inserted into a blood vessel, and the guide wire is used to guide the catheter to the vicinity of the target stenosed part in a blood vessel.

The guide wire used in the PTCA process is inserted in a blood vessel together with the catheter, with the distal end portion of the guide wire being protruded from the distal end of the catheter, to the vicinity of the target stenosed part in a blood vessel, and guides the distal end portion of the catheter to the target stenosed part. The distal end portion of the catheter has various shapes according to the purpose and the location in the body for which the catheter is designed, and has a flexibility which allows the catheter to follow complicated shapes of blood vessels and other organs in the body.

Since blood vessels bend in a complicated manner, a guide wire used to insert a catheter into a blood vessel must have a proper flexibility, pushability and torque-transmitting capability (operatability is a generic term for these two properties in combination), and kink resistance (property which resists sharp bending). A guide wire can have a metal coil with an appropriate flexibility attached around the distal end portion of a small-diameter core material to provide a proper amount of flexibility, or the guide wire can use a wire of a super elastic alloy such as Ni-Ti as the core material.

Conventional guide wires have a core material formed of substantially a single material, and a material with a relatively high rigidity is used to increase the operatability of the guide wire. As a result, the distal end portion of guide wire does not have a sufficient flexibility. On the other hand, if a material with a relatively low rigidity is used to increase the flexibility of the distal end portion of the guide wire, the operatability of the proximal end portion decreases. Therefore, it has been thought that is difficult to satisfy both the requested flexibility and operatability with a single core material.

To solve this problem, a guide wire is known which uses a core material formed of Ni-Ti alloy, for example, and having its distal end portion heat-treated and proximal end portion in different conditions to increase the flexibility of the distal end portion and the rigidity of the proximal end portion. However, there is a limitation of the control of flexibility by such heat treatment; it is not always possible to give the proximal end portion a satisfactory rigidity while making the distal end portion sufficiently flexible.

A guide wire made by joining a Ni-Ti alloy wire and a stainless steel wire with a tubular connector of Ni-Ti alloy to satisfy the desired flexibility for the distal end portion and a high rigidity for the proximal end portion is disclosed in Japanese Patent Application Laid Open No. 1992-9162. Since the tubular connector of Ni-Ti alloy used in this invention has a uniform rigidity over the entire length, there is a relatively large difference in the rigidity between the Ni-Ti alloy wire and the stainless steel wire which have different rigidities. As the result, a stress concentration occurs at the joint of the Ni-Ti alloy wire and the stainless steel wire, which can cause kink or decrease the operatability.

SUMMARY OF THE INVENTION

Therefore, the first object of this invention is to provide a guide wire which has high operatability and kink-resistance improved by making the change in the rigidity along the length smooth.

Further, the strength of connection between the first wire and the connector which are formed of a super elastic alloy is increased from the point of view of safety though the guide wire disclosed in Japanese Patent Application Laid Open No. 1992-9162 has satisfactory properties for a guide wire.

The second object of this invention is to provide a guide wire whose first wire and connector can be joined with an adequate strength if the first wire and the connector are formed of different materials and which has an increased safety during use.

The first object is attained by a guide wire which comprises a first wire which is located at the distal end of the guide wire and has an appropriate elasticity, a second wire which is located of the proximal end of the guide wire and has a flexural rigidity greater than that of said first wire, and a tubular connector for joining said first and second wires, and characterized in that said connector has grooves or slits or both formed in its portion on the distal side of a boundary between said first wire and said second wire.

The second object is attained by a guide wire which comprises the first wire which is located on the distal end of the guide wire and has an appropriate elasticity, the second wire which is located on the proximal end of the guide wire and has a flexural rigidity greater than that of said first wire, and a tubular connector for joining said first and second wires, and characterized in that said connector is formed of a material different from the material of said first wire, that the proximal portion of said first wire joined to said connector is provided with a thin metal coating as an adjuvant to joining, and that said first wire is joined to said connector by the portion provided with the thin metal coating by brazing.

BRIEF DESCRIPTION OF THE DRAWINGS

FIGS. 4(1)–4(2) are diagrams showing the points of measurement of the flexural rigidity on and around the connector of the guide wire of this invention, and those on and around the connector of the comparison guide wire.

DETAILED DESCRIPTION OF PREFERRED EMBODIMENTS

Next, the guide wire of this invention is described below in detail by use of preferred embodiments with reference to the accompanied drawings.

Figure 1:
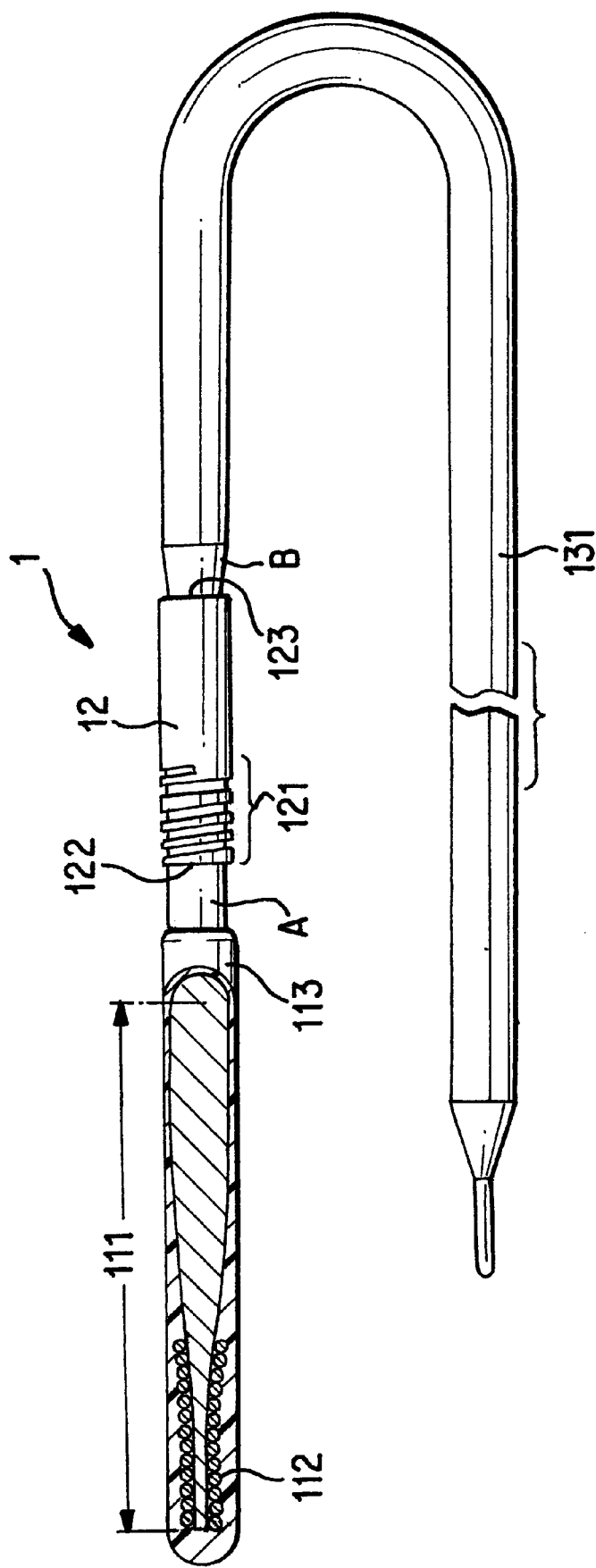
FIG. 1 is a diagram showing an embodiment of the guide wire of this invention.

FIG. 1 is a side view of the entire guide wire of this invention.

A guide wire 1 comprises a first wire A located at the distal end of the guide wire and having an appropriate elasticity, a second wire B located at the proximal end of the guide wire and having a flexural rigidity greater than that of said first wire and a tubular connector 12 for joining the first and second wires A,B. The connector 12 has a groove (or grooves) or a slit (or slits) or both of them formed in its portion on the distal side of a boundary 124 between the first wire A and the second wire B.

The guide wire 1 of this invention has a wire main body (core wire) which is the main component of the guide wire 1. The wire main body consists of the first wire A at the distal end of the guide wire and the second wire B at the proximal end of the guide wire. The proximal end of the first wire A and the distal end of the second wire B are connected by being fitted in a tubular connector 12.

The first wire A is a wire with elasticity. There is no special condition for the material for the first wire A, and various plastics and metals can be used. A super elastic alloy is preferable. By this construction, it becomes possible to endow the distal end portion of the wire main body with high operatability and kink-resistance without increasing the diameter of the first wire A.

A super elastic alloy here means an alloy which exhibits super elasticity at the temperature at which it is used (body temperature, or around 37° C.). Super elasticity is the property possessed by certain alloys that allows them to return to their original shape after having been deformed (bent, extended, or compressed) to an extent such that normal metals are subjected to a plastic deformation.

The preferable composition of the super elastic alloy is Ni-Ti alloy with 49 to 58 atomic percent of Ni, Cu-Zn alloy with 38.5 to 41.5 weight percent of Zn, Cu-Zn-X alloy (X is at least one of Be, Si, Sn, Al, or Ga), or Ni-Al alloy with 36 to 38 atomic percent of Al. Of these alloys Ti-Ni alloy is most preferable.

The second wire B is also a wire with elasticity. There is no special condition for the material for the second wire B. Various plastics and metals which have higher rigidity than the first wire A, especially metals, are used. By this construction, it becomes possible to endow the wire main body with high operatability and kink-resistance without increasing the diameter of the second wire B.

The outside diameter of the second wire B may be larger than that of the first wire A in order to increase the operatability and kink-resistance (see the second wire B in FIG. 1). When using the second wire B with the outside diameter larger than that of the first wire A, the portion of the second wire B fitted in the tubular connector 12 is preferably formed so as to be equal to that of the portion of the first wire A fitted in the tubular connector 12.

The preferable metallic material for the second wire B is a stainless steel or piano wire, for example. The most preferable metallic material is a stainless steel with a high rigidity.

The tubular connector 12 has elasticity and is formed in the shape of a tube with the opening 122 in which the first wire A is inserted and the second opening 123 in which the second wire B is inserted; the openings 122 and 123 connect with each other.

By using a connector 12 in the shape of a tube, connection of the first wire A and the second wire B becomes easier, and the bending rigidity is made uniform in all radial directions.

There is no special condition for the material for the tubular connector 12, and various plastics and metals can be used as for the first wire A and the second wire B. The tubular connector 12 is preferably made of a material whose rigidity is greater than that of the first wire A, and more preferably made of the same or same kind of material as the second wire B.

The super elastic alloy can be used as for the tubular connector 12. The preferable composition of the super elastic alloy used for the tubular connector 12 is above-described Ni-Ti alloy, Cu-Zn alloy, Cu-Zn-X alloy (X is at least one of Be, Si, Sn, Al, or Ga), Ni-Al alloy, or stainless steel.

When the rigidity of the tubular connector 12 is smaller than that of the first wire A, the rigidity of the portion of the wire main body covered by the tubular connector 12 is for the most part determined by the rigidity of the portion of the first wire A held in the tubular connector 12 and that of the portion of the second wire B held in the tubular connector 12, causing a large change in rigidity at the boundary 124 of the first wire A and the second wire B.

When the rigidity of the tubular connector 12 is greater than that of the second wire B, on the other hand, the rigidity of the portion of the wire main body covered by the tubular connector 12 is for the most part determined by the rigidity of the tubular connector 12 itself. As the result the change in rigidity at the boundary of the first wire A and the second wire B becomes smaller, but the change in rigidity at the distal end of the tubular connector 12 on the first wire A and that at the proximal end of the tubular connector 12 on the second wire B become larger instead. Since a stress concentration occurs at the positions at which there is a large change in rigidity, the mechanical energy (or movement of the proximal end portion) is not transmitted smoothly to the distal end portion, and the operatability and kink-resistance decrease.

Especially, the material with about the same rigidity as the second wire B is preferable in order that the flexural rigidity of the wire main body can be smoothed to change gradually from the rigidity of the first wire A to that of the second wire B by the tubular connector 12, because the rigidity of the tubular connector 12 can be easily made smaller by processing.

Further, in order to make connection of the tubular connector 12 with the first wire A or second wire B easy, the material for the tubular connector 12 is preferably the same or the same kind of metal as that for the first wire A or second wire B. The material for the tubular connector 12 is more preferably the same or the same kind of metal as that for the first wire B.

The wall thickness of the tubular connector 12 between the interior surface and the exterior surface is preferably within the range of 0.02 to 0.06 mm, and more preferably 0.03 to 0.05 mm in order to make the wire main body have a necessary and sufficient strength and operatability.

In this invention, the connector 12 is provided with means for making the rigidity of the connector 12 change smoothly and gradually from the rigidity of the first wire A to that of the second wire B. Specifically, it is preferable to form a helical slit or groove in the first wire-receiving portion 121 of the connector 12, as shown in (1) and (2) in FIG. 2. This slit or groove decreases the rigidity of the connector 12.

Figure 2:
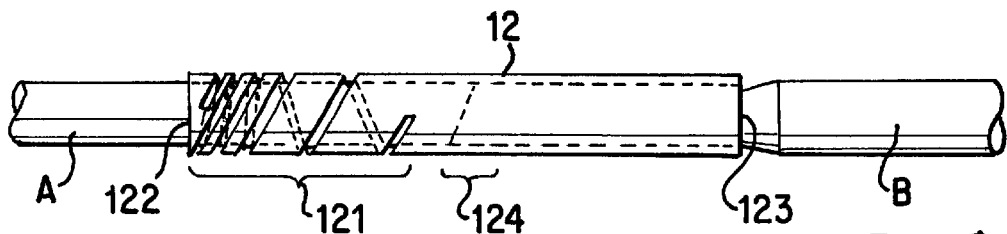
FIGS. 2(1)–2(5) are diagrams showing examples of the slits or grooves formed in the connector of the guide wire of this invention.
Figure 2:
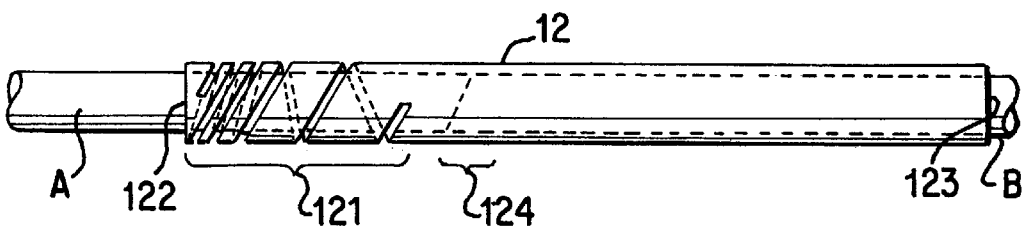
Figure 2:
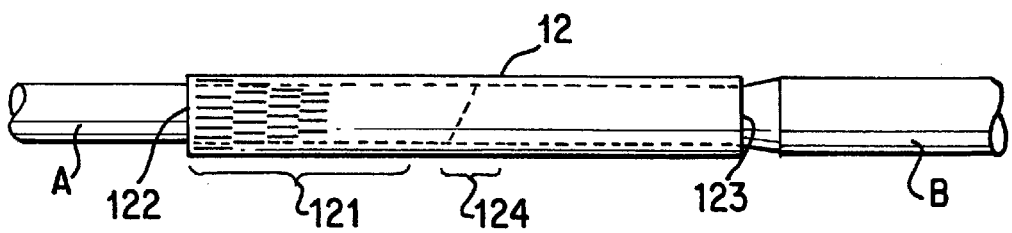
Figure 2:
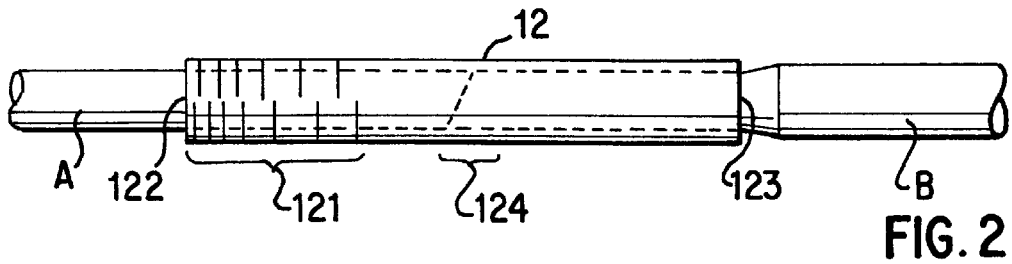
Figure 2:
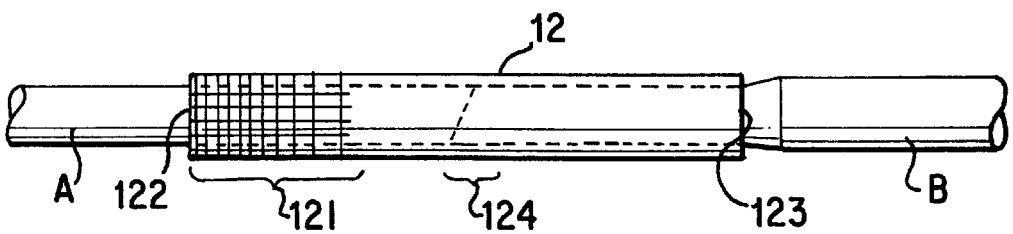

Further, slits or grooves in other shapes or arrangements may also be formed in the first wire-receiving portion 121 of the connector 12 as shown in FIG. 2; slits or grooves parallel to the axis ((3) in FIG. 2), those perpendicular to the axis ((4) in FIG. 2), and those in a grid ((5) in FIG. 2), for example.

Grooves may be formed in either the exterior surface or the interior surface of the first wire-receiving portion 121 of the tubular connector 12. Both slits and grooves may be formed though not shown in FIG. 2. It is not preferable that slits or grooves are formed across the boundary 124 between the first wire A and the second wire B. In other words, the slit or groove is located on the proximal end of the first wire A and is not positioned on the distal end of the second wire B.

Forming slits or grooves over the boundary 124 between the first wire A and the second wire B causes a decrease of the flexural rigidity at the boundary 124 and makes the guide wire prone to kink.

Figure 3:
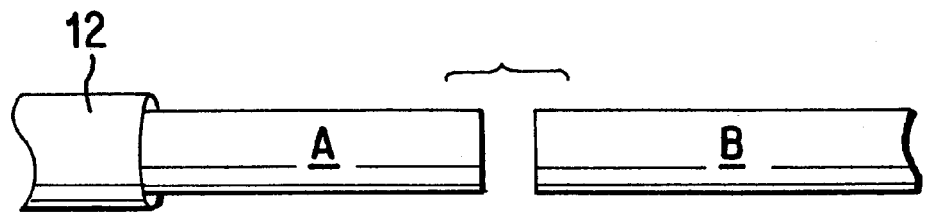
FIGS. 3(1)–3(5) are diagrams showing examples of connecting methods for the guide wire of this invention.
Figure 3:
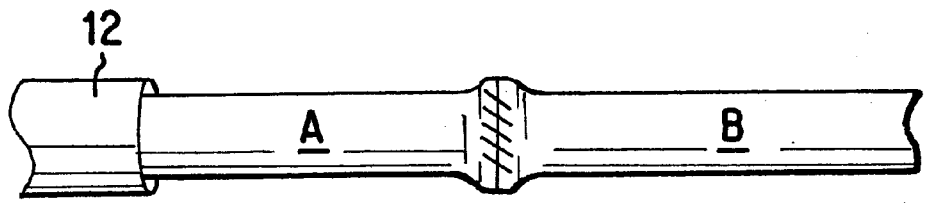
Figure 3:
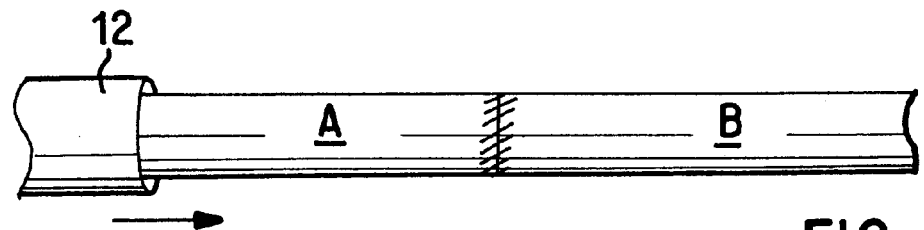
Figure 3:
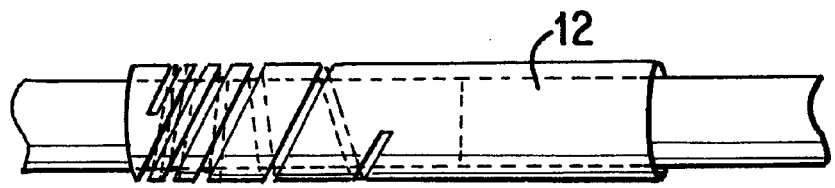
Figure 3:
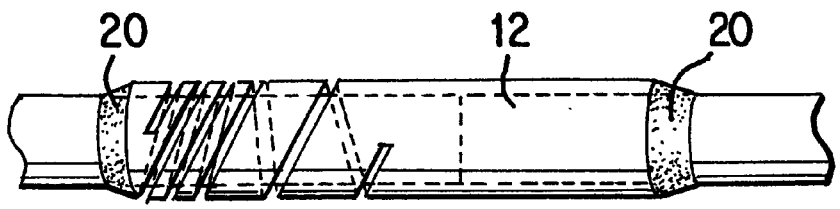

These slits and grooves change the flexural rigidity of the portion in which they are formed according to their interval or pitch. Therefore, it is possible to change the flexural rigidity smoothly from the flexural rigidity of the first wire A to that of the second wire B by using a material having the same rigidity as that of the second wire B and forming slits or grooves in the interval or pitch which becomes smaller toward the end of the tubular connector 12 on the first wire A side (distal end) and becomes larger toward the boundary 124 as shown in FIGS. 1 to 3.

The pattern (shapes and arrangement) of the slits and grooves is not limited to those shown in the Figures as a matter of course.

It is preferable that the distal end portion 111 of the first wire A has an X-ray contrast material attached and is provided with a smooth coating of a synthetic resin or polymer material such as plastics so as to make the tip round. By thus using an X-ray contrast material, the location of the distal end of the guide wire can be viewed on a monitor screen. The synthetic resin or polymer material coating 113 prevents the guide wire 1 from causing damage to the interior wall of a blood vessel by scraping.

It is preferable that the distal end portion of the first wire A becomes gradually smaller in exterior diameter toward the distal end. By thus making the exterior diameter of the distal end portion of the first wire A gradually smaller toward the distal end, it becomes possible to make the exterior diameter of the distal end portion 111 uniform when the X-ray contrast material 112 is attached to the distal end portion 111 and the distal end portion 111 is covered with the coating. The guide wire 1 of this construction can be inserted to an intended position easily and safely passing through the complicated shapes of branching and bending blood vessels.

The X-ray contrast material 112 may be a coil of wire of an X-ray opaque material such as Au or Pt which is wound on the distal end portion of the first wire A and buried in the coating 113, for example.

For the polymer material for the coating 113, polyethylene, poly(vinyl chloride), polyester, polypropylene, polyamide, polyurethane, polystyrene, polycarbonate, silicone rubber or other various elastomers, or a composite of these materials is preferable, and a material that has an elasticity equal to or smaller than that of the first wire A is especially preferable.

Further, it is preferable to form a layer of a hydrophilic macromolecule substance which exhibits luburicity in wet condition (not shown). This layer of a hydrophilic substance reduces the friction, making insertion of the guide wire 1 easier and hence improving the operatability and safety for insertion.

Hydrophilic macromolecule substances usable to form the hydrophilic layer are divided into natural macromolecule substances (starch, cellulose, tannin-lignin, polysaccharide, protein, for example) and synthesized macromolecule substances (PVA, polyethylene oxide, acrylic acid, maleic anhydride, phthalic acid, water-soluble polyester, ketone aldehyde, (meth) acrylamide, polyamine, polyelectrolyte, water-soluble nylon, acrylic acid glycidyl acrylate).

Of the above substances, celluosic macromolecule (hydroxypropyl cellulose, for example), polyethylene oxide macromolecule (polyethylene glycol), maleic anhydride macromolecule (maleic anhydride copolymer such as methyl vinyl ether-maleic anhydride copolymer), acrylamide macromolecule (poly(dimethylacrylamide), for example), water-soluble nylon (AQ-nylon P-70 produced by Toray Industries Inc., for example), or their derivatives are preferable because their property of reliably reducing coefficient of friction in blood. Reduction of coefficient of friction by a layer of a hydrophilic macromolecule substance is described in detail in the specification of Patent Application Laid Open No. 1997-84871.

It is preferable that the second wire B is subjected to a treatment for reducing the friction which occurs from contact with the interior wall of the catheter used along with the guide wire 1. Specifically, this is attained by just coating the proximal end portion (basal portion) 131 at which the second wire B comes in contact with the interior wall of the catheter with a substance whose coefficient of friction is low against the material of the interior wall of the catheter (fluororesin such as polytetrafluoroethylene or silicone, for example). By thus reducing the friction against the catheter, the operatability of the second wire B held in the catheter can be maintained without decreasing.

Although there is no particular limitation to the diameters of the first wire A, connector 12, and second wire B, the diameters (in average value) are preferably about 0.25 to 0.65 mm (0.010 to 0.025 inches), and more preferably about 0.36 to 0.45 mm (0.014 to 0.018 inches) for a guide wire used for insertion of a catheter for PTCA operation.

There is also no particular limitation on the method of connecting the first wire A and the second wire B by means of the connector 12. It is preferable to join the first wire A with the connector 12 and the second wire B with the connector 12, respectively. For example, the end surface of the first wire A cut at a predetermined angle (θ) to the axes of the first and second wires A and B and the end surface of the second wire B cut in the same manner are put in contact with each other in the connector 12 and joined together. The angle θ is θ≦90°, preferably 0°<θ≦45°, and more preferably 0.5°≦θ≦20°. By cutting the end surfaces of the first wire A and the second wire B at this angle with the axes of the first wire A and the second wire B, the change in the flexural rigidity at the end surfaces in contact with each other can be made smaller and hence the kink resistance increases.

There is no particular condition for the method of joining, and ordinary methods such as spot welding by laser light can be used. There is also no particular condition for the locations to be welded, as long as the locations extend over both sides of the boundary 124. Welding may be made over the entire length of the connector 12 or only over the regions near the boundary 124 (excluding the region in which grooves or slits are formed). It is also possible to fix both ends by an adhesive agent. Further, the strength of the joint increases by joining by making use of the above-described grooves formed in the interior surface or slits.

As the wall thickness of the connector 12 decreases within a certain limit, the connector 12 melts more easily and the weldability increases. Therefore, the thickness of the connector 12 is preferably within the above-described range.

When forming the connector 12 of a stainless steel which is a material with a high rigidity, the wall thickness of the connector 12 can be made thin, and hence the joinability, especially weldability, of the connector 12 to the first wire A increases. Further, when forming the connector 12 of the same stainless steel as the second wire B, a high weldability between the connector 12 and the second wire B can be obtained because of their same compositions.

This connection can also be made by caulking. Caulking can be easily performed by firmly pushing the first wire A and the second wire B into the connector 12 from the opposite ends and applying pressure to the portion at and around the boundary 124 from outside. This caulking may be used together with welding described above. To increase the joinability by caulking, the abutting end surfaces of both wires A and B are preferably oblique as described above. When being pressed so as to come into contact with each other, the end surfaces of both wires A and B shift in the opposite directions with respect to the axis at the boundary 124 because of the obliqueness of the end surfaces. This causes projections to form, and caulking is done by the expansive force from inside the connector 12. Making the end surfaces of both wires A and B has another effect of making the change in the rigidity at the boundary 124 gradual.

FIG. 3 shows another connecting method and the procedure.

This Figure shows steps (1) to (5) of butt seam welding which is one variation of butt resistance welding.

In step (1), the first wire A and the second wire B set on a butt welding machine (not shown) are shown. A connector 12 is put on the proximal-side portion of the first wire A in advance.

In step (2), the first wire A and the second wire B are moved by a butt welding machine toward each other to press the proximal end surface of the first wire A and the distal end surface of the second wire B into contact with each other, with a predetermined voltage being applied to the first wire A and the second wire B. A layer of melted metal is formed at the end surfaces held in pressured contact with each other, and the first wire A and the second wire B are firmly joined.

In step (3), a projection formed by pressured contact around the joint is scraped off so that the connector 12 can be fitted over the joint.

Next in step (4), the connector 12 is slid over the joint.

In step (5), the connector 12 is bonded to the first wire A and the second wire B at its ends by means of a predetermined adhesive 20.

The first wire A and the second wire B can be joined by not only above-described spot welding, but also butt seam welding (butt resistance welding) as shown above.

Further, the connecting method is not limited to the above-described methods, and other methods such as brazing (soldering) and bonding with an adhesive can is be used.

The improved operatability and kink-resistance of the guide wire 1 described above will become evident by the measurement of the flexural rigidity described below.

FIG. 4 shows the points of measurement of the flexural rigidity of the connector 12 and its vicinity of the guide wire of this invention and those of a comparison guide wire.

Here, the first wire A used for the guide wire 1 is formed of the aforementioned Ti-Ni alloy, and the connector 12 and the second wire B are formed of the aforementioned stainless steel. On the other hand, guide wire 10, which is a comparison example, has the same construction as the guide wire 1, except that slits are not formed in the connector 12.

The points of measurement of the flexural rigidity are indicated by arrows 1' to 14' shown in FIG. 4. The arrows 1' to 13' are set at 5 mm intervals. Only the arrow 14' is a point of measurement of the flexural rigidity of the second wire B.

Measurement of the flexural rigidity was conducted by putting fulcrums at the positions ½ inches on both sides of each point of measurement of the guide wires 1 and 10 (arrows 1' to 14') and then measuring the load needed to press down the point of measurement between the fulcrums 2 mm.

The arrows 1' and 2' of the guide wire 1 indicate the points of measurement of the flexural rigidity on the first wire A. The arrows 3' to 10' indicate the points of measurement of the flexural rigidity on the slit-formed region in the first wire-receiving portion of the connector 12. The arrow 11' indicates a point of measurement of the flexural rigidity on the no-slit region in the first wire-receiving portion of the connector 12. The arrow 12' indicates the boundary 124. The arrow 13' indicates a point of measurement of the flexural rigidity on the second wire-receiving portion of connector 12. The arrow 14' indicates a point of measurement of the flexural rigidity on the second wire B (the large-diameter portion).

The arrows 1' and 2' of the guide wire 10 indicate points of measurement of the flexural rigidity of the first wire A. The arrows 3' to 11' indicate points of measurement of the flexural; rigidity of the portion of the connector 12 enclosing the first wire A in which no slits are formed. The arrow 12' indicates the boundary 124. The arrow 13' indicates a point of measurement of the flexural rigidity of the portion of connector 12 enclosing the second wire B. The arrow 14' indicates a point of measurement of the flexural rigidity of the second wire B (larger-diameter portion).

Table 1 shows the flexural rigidities measured at the points indicated by arrows (1' to 14') on the guide wires 1 and 10.

TABLE 1

| Arrow | 1' | 2' | 3' | 4' | 5' | 6' | 7' |
|---|---|---|---|---|---|---|---|
| Guide Wire 10 (g) | 8.0 | 8.0 | 52.1 | 52.1 | 52.1 | 52.1 | 52.1 |
| Guide Wire 1 (g) | 8.0 | 8.0 | 8.6 | 9.0 | 12.0 | 15.0 | 18.2 |
| Arrow | 8' | 9' | 10' | 11' | 12' | 13' | 14' |
| Guide Wire 10 (g) | 52.1 | 52.1 | 52.1 | 52.1 | 54.6 | 62.0 | 72.5 |
| Guide Wire 1 (g) | 24.2 | 38.8 | 44.7 | 50.1 | 54.6 | 62.0 | 72.5 |

Figure 5:
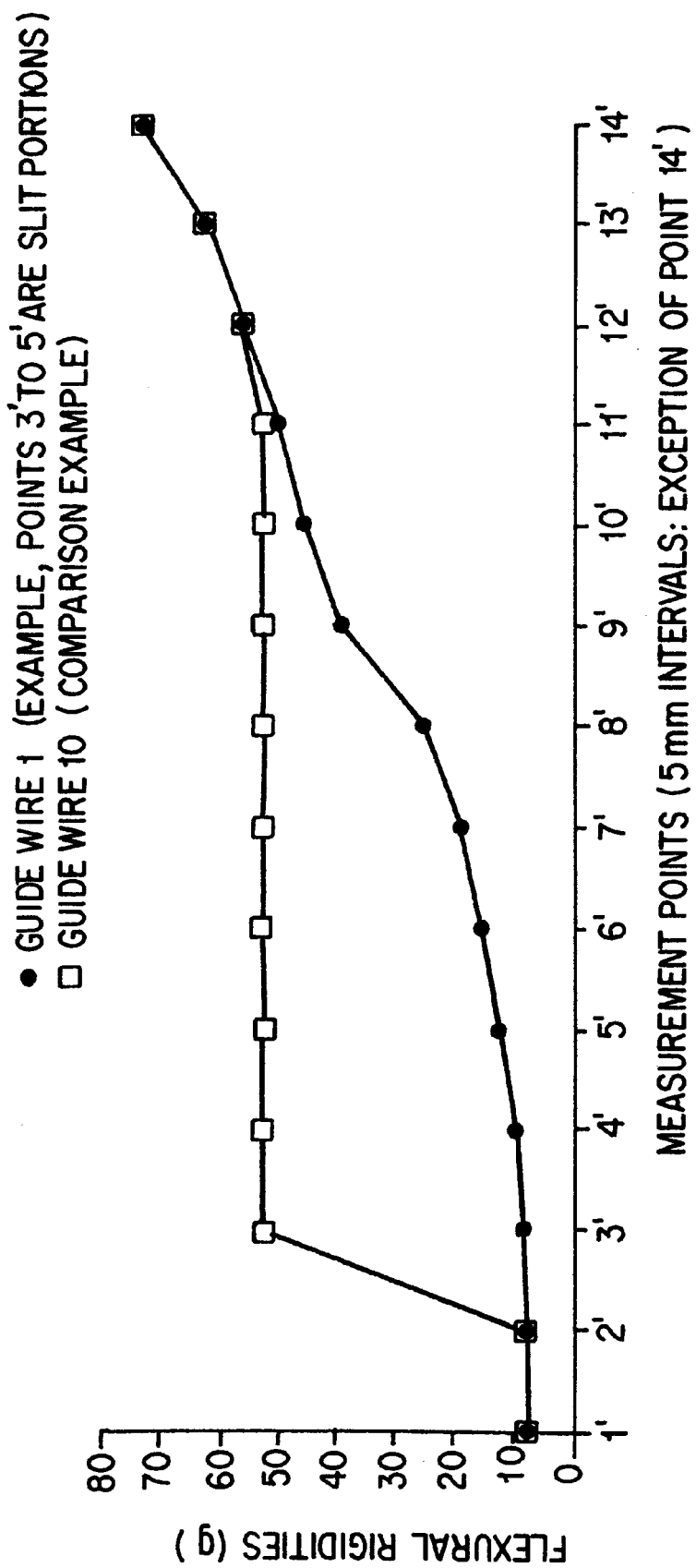
FIG. 5 is a graph showing the result of measurement of the flexural rigidity.

FIG. 5 shows the measured flexural rigidities on Table 1 in a graph. Flexural rigidities (g) are shown on the vertical axis of the graph, and the points of measurement of the flexural rigidity are shown on the horizontal axis by the arrow numbers 1' to 14'.

The following conclusions are obtained from the measured flexural rigidities.

(1) Guide Wire 1

By forming slits in such a manner that the pitch of the slits changes from a large density (arrow 3') to a small density, the flexural rigidities measured at points 3' to 10' change gradually and smoothly from the flexural rigidity of the first wire A to that of the no-slit region of the first wire-receiving portion of the connector 12; the measured flexural rigidities further change gradually and smoothly to the flexural rigidity at point 14' through that at point 13'. It can be understood from this result that the guide wire 1 bends smoothly without kinking when bent.

(2) Guide Wire 10

There is a large difference between the flexural rigidities at points 2' to 3', and therefore it can be known that the guide wire 10 is prone to bend at a sharp angle when bent.

The torsional rigidities of the guide wires 1 and 10 have similar tendencies to the flexural rigidities.

The same measurement was made by forming grooves instead of the slits in the connector 12, and the same results were obtained.

In this guide wire 1 of this invention, the rigidity of the connector 12 thus can be made to change smoothly from the rigidity of the first wire A to that of the second wire B. Specifically, a large change in the rigidity is divided into smaller changes in the connector 12, and thereby the concentration of stress is reduced. This results in the improved operatability and kink-resistance of the guide wire 1 in comparison to the guide wire 10.

Figure 6A:
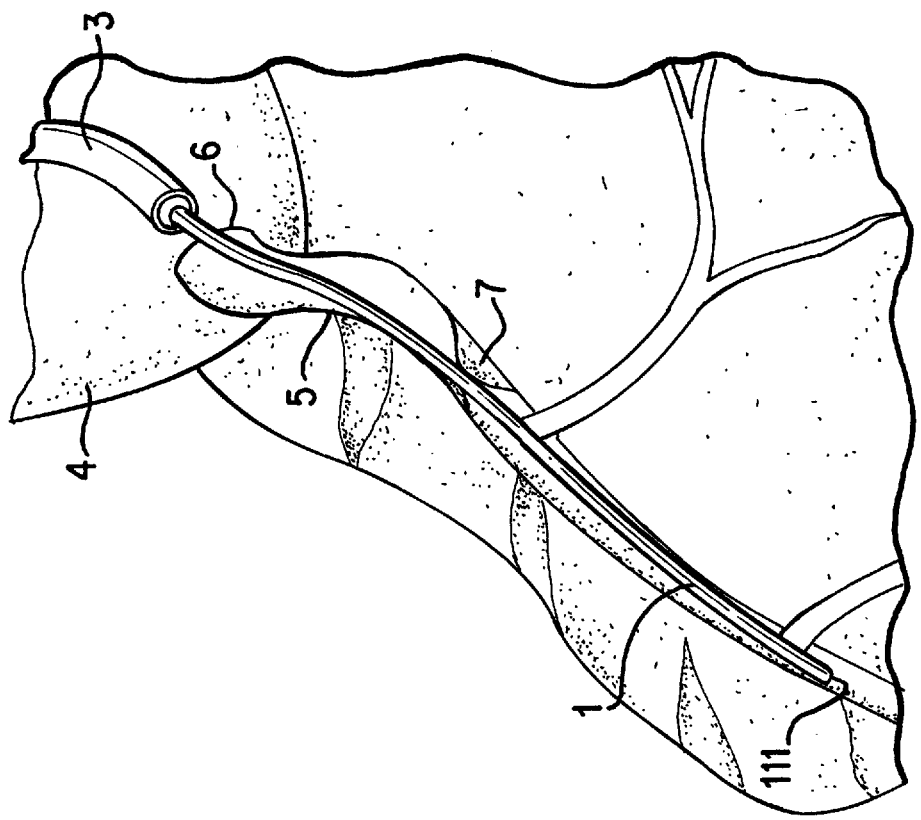
FIG. 6 is a diagram showing an example of use of the guide wire of this invention.
Figure 6:
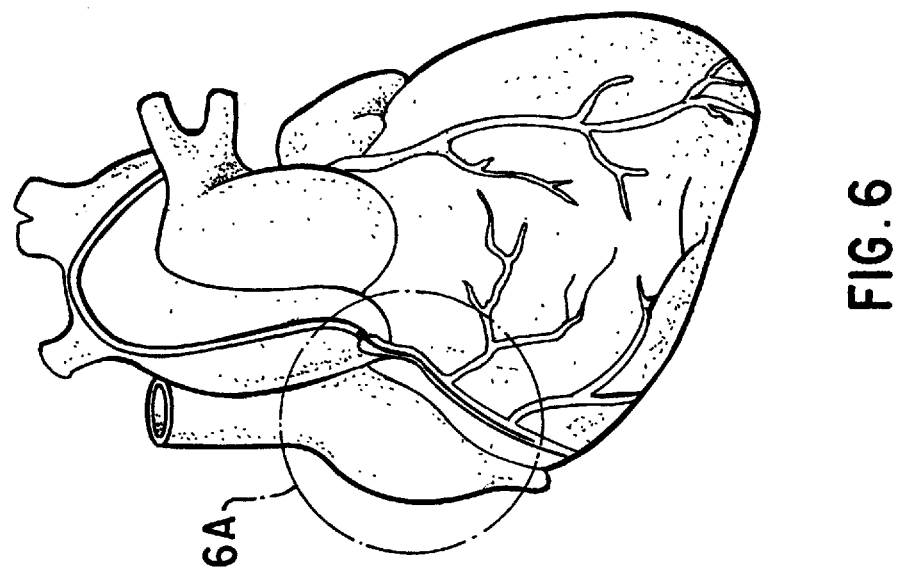
Figure 7:
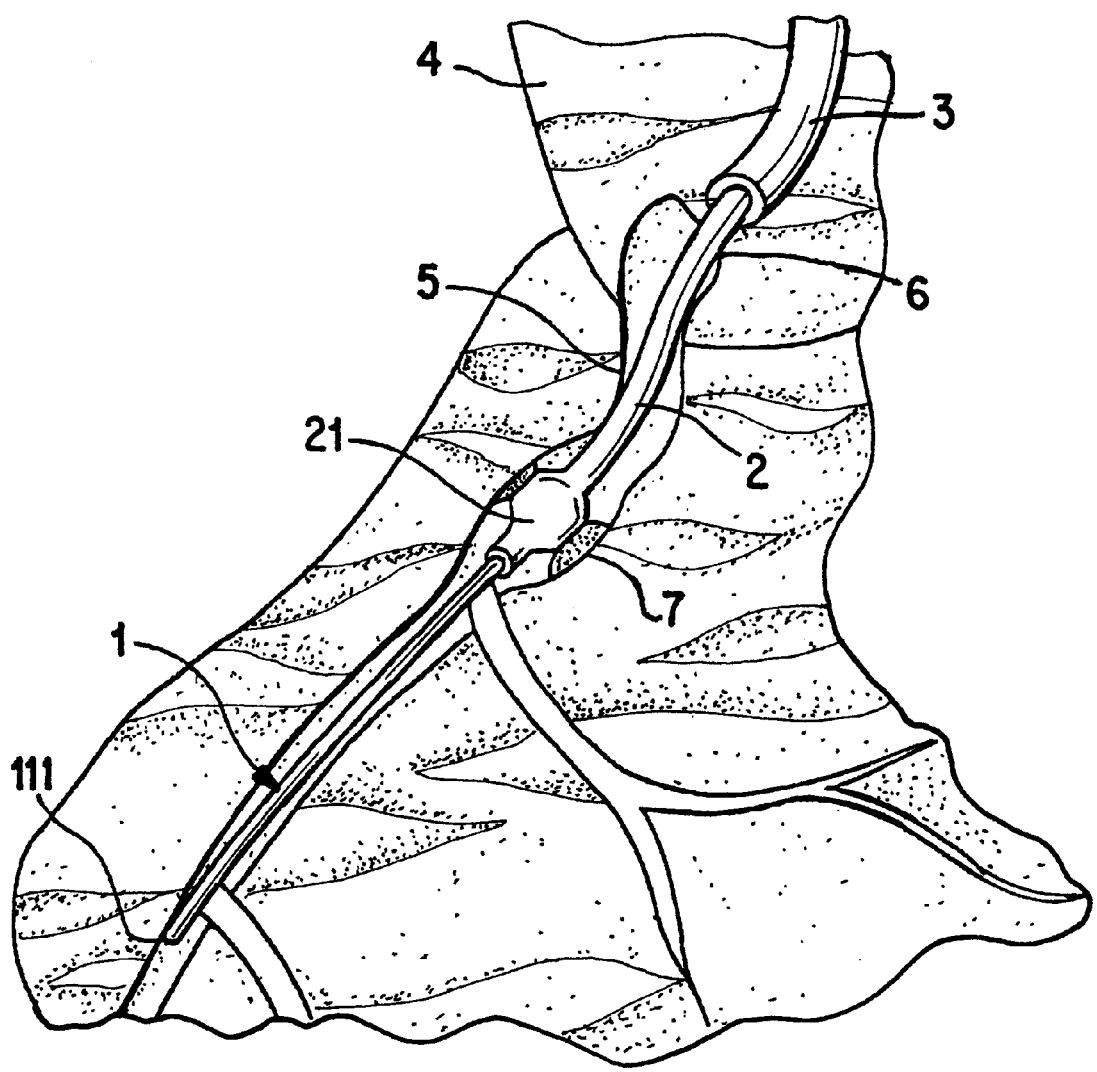
FIG. 7 is a diagram showing an example of use of the guide wire of this invention.

FIGS. 6 and 7 illustrate the manner the guide wire of this invention is used in the PTCA process.

In FIGS. 6 and 7, indicated by reference number 4 is the aortic arch, 5 is the right coronary artery of a heart, 6 is the right coronary artery ostium, and 7 is the target stenosed part. Indicated by the reference number 3 is a guiding catheter to introduce the guide wire 1 from the arteria fermoralis into the right coronary artery. Indicated by 21 is a balloon catheter equipped on the distal end portion with an expandable and contractible balloon for dilating a stenosed part.

As shown in FIG. 6, the distal end portion of the guide wire 1 is made to protrude from the distal end of the guiding catheter 3 and inserted from the right coronary artery ostium 6 into the right coronary artery 5 of the heart. The guide wire 1 is further advanced and inserted into the right coronary artery with the distal end leading, and then stopped at the position where the distal end is advanced beyond the stenosed part 7 of a blood vessel. A path for the balloon catheter 2 is thus secured.

Next, as shown in FIG. 7, the distal end of the balloon catheter 2 is advanced beyond the distal end of the guiding catheter 3, further advanced over the guide wire 1 to be introduced from the right arteria fermoralis 6 into the right coronary artery 5 of the heart, and stopped at the position where the balloon is placed in the stenosed part.

Next, a fluid is injected into the balloon from the proximal side of the balloon catheter 2 to inflate the balloon 21, and the stenosed part is dilated by the inflated balloon. Plaque deposited on the arterial wall, such as cholesterol, is thus physically compressed against the arterial wall, and blocking of blood flow is eliminated.

Although the guide wire of this invention is described above using embodiments shown in Figures, this invention is not limited to these embodiments. For example, the first wire A and the second wire B constituting the wire main body may be either solid or hollow, and may be formed of various resin materials such as polyimide, polyester, polyolefin (polypropylene, polyethylene, etc.), fluororesin, and polyurethane, in addition to metals such as aforementioned super elastic alloy, piano wire, stainless steel, and tungsten. The wire main body may also be formed of wires which are made of two or more layers of different materials or properties.

In the guide wire of this invention, as described above, the connector is made to have a smoothly changing rigidity by forming grooves and/or slits in its portion on the proximal side of the boundary between the first wire and the second wire.

Especially, by forming the groove and/or slits so that their density increases toward the distal end of the connector 12, the rigidity of the guide wire can be made to increase smoothly from the distal end portion of the first wire to the boundary between the first wire and the second wire.

Further, by forming the second wire of a metal whose rigidity is greater than that of the first wire and by forming the connector of the same or same kind of material as the second wire so as to have a gradually changing rigidity, the rigidity of the guide wire can be made to increase smoothly from the proximal end portion of the first wire to the distal end portion of the second wire.

Further, by forming the first wire of a super elastic metal and the second wire of a stainless steel, a guide wire which has the distal end portion with a good flexibility and the proximal end portion with a high rigidity and has a gradually changing rigidity can be obtained.

Further, by fixing the first wire and the connector, and the second wire and the connector, respectively, by welding, the strength of connection between the first wire and the second wire can be increased. A high weldability can be obtained by using appropriate materials for both wires and the connector.

In addition, by making the abutting end surfaces of the first wire and the second wire oblique to a surface perpendicular to the axes of both wires, the change in the rigidity at and around the boundary can be made smoother, and the strength of connection of the first and second wires can be increased.

By thus forming the tubular connector of a suitably selected material and forming grooves or slits in the connector, this invention divides the difference between the rigidities of the first wire and that of the second wire into smaller differences in the connector and thereby distributes the stress. Therefore, the transmission of mechanical energy from the proximal end portion to the distal end portion is made smoother, and hence this invention can provide a guide wire which has high operatability and kink resistance.

Next, a guide wire 51 of another embodiment of this invention is explained below in detail with reference to drawings.

Figure 8:
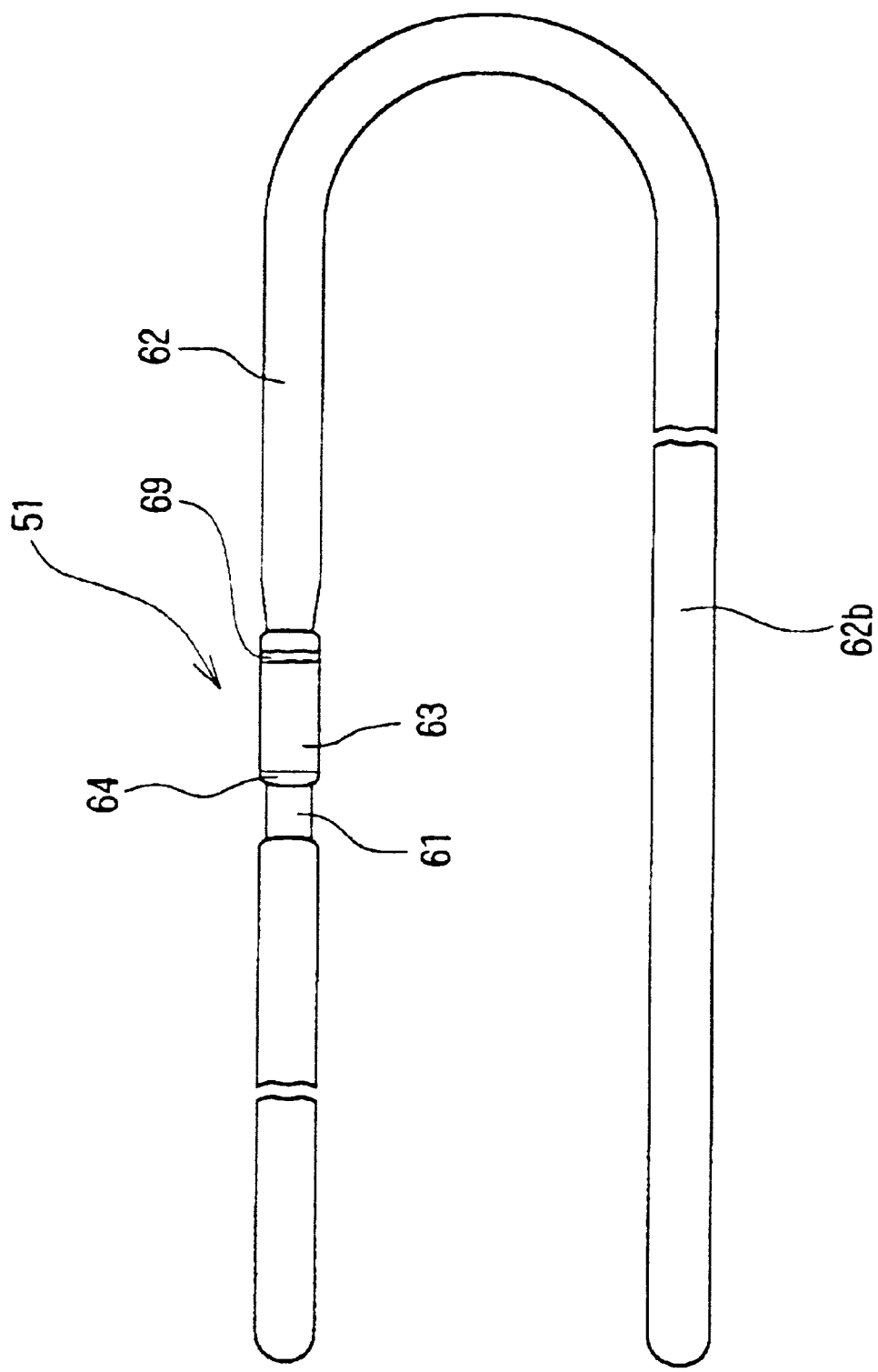
FIG. 8 is a plan view of the guide wire of this invention.
Figure 9:
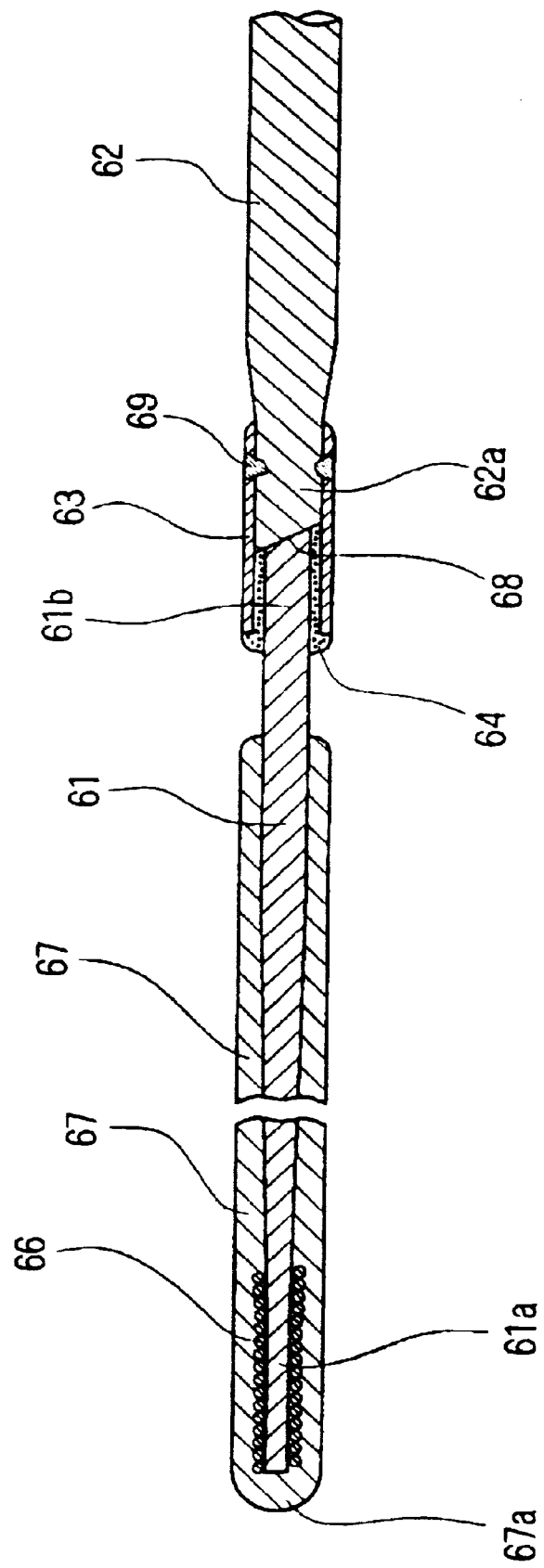
FIG. 9 is a sectional view of the distal end portion of the guide wire shown in FIG. 8.
Figure 10:
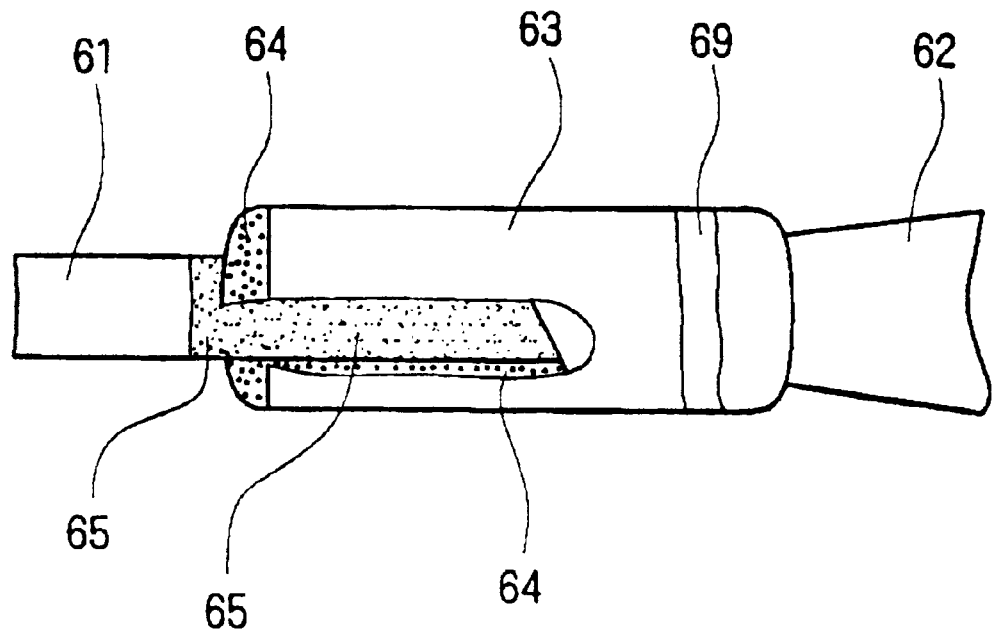
FIG. 10 is a partly-broken, enlarged external view of the connector and its vicinity of the guide wire shown in FIG. 8.
Figure 11:
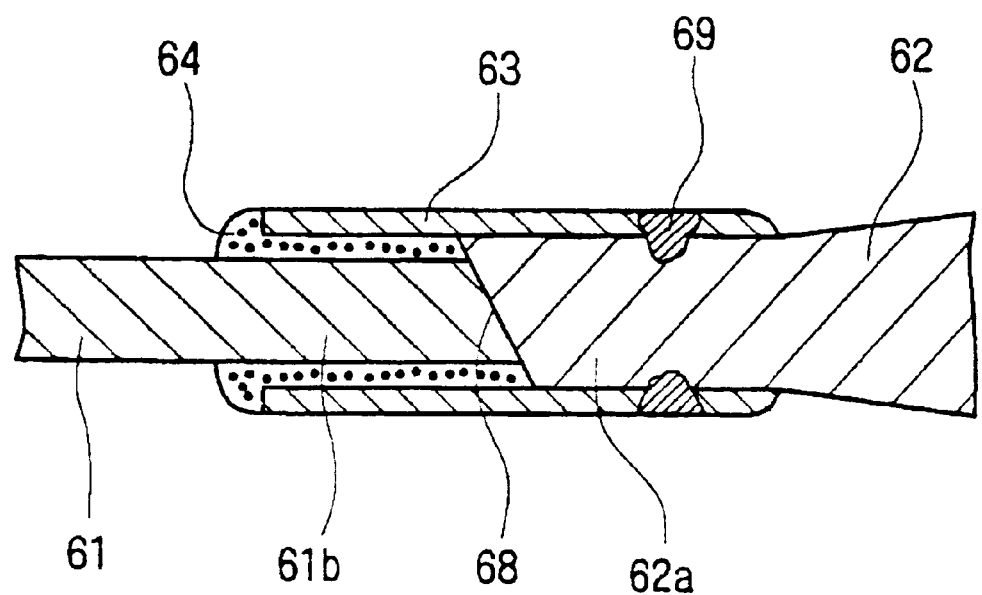
FIG. 11 is an enlarged sectional view of the connector and its vicinity of the guide wire shown in FIG. 8.

FIG. 8 is a plan view of the guide wire 51 of this invention. FIG. 9 is a sectional view of the distal end portion of the guide wire 51 shown in FIG. 8. FIG. 10 is a partly-broken, enlarged external appearance of the connector 63 and its vicinity of the guide wire 51 shown in FIG. 8. FIG. 11 is an enlarged sectional view of the connector 63 and its vicinity of the guide wire 51 shown in FIG. 8.

The catheter guide wire 51 of this invention comprises the first wire 61 which is disposed at the distal end of the guide wire and has flexibility, the second wire 62 which is disposed at the proximal end of the guide wire and has rigidity greater than that of the first wire 61, and a connector 63 for connecting the first wire 61 and the second wire 62. The connector 63 is formed of a material different from the first wire 61. The proximal end portion of the first wire 61 is connected to the connector 63 is provided with a thin metal coating 65 for aiding connection. The first wire 61 is joined by brazing to the connector 63 by the portion provided with the thin metal coating 65.

The guide wire 51 of this invention has a wire main body (core) as the main component of the guide wire 51. This wire main body consists of the first wire 61 which forms the distal part of the wire main body and the second wire 62 which forms the proximal part of the wire main body. The proximal end portion 61b of the first wire 61 and the distal end portion 62a of the second wire 62 are inserted in and connected with the tubular connector 63.

The first wire 61 is a wire with flexibility. There is no special condition for the material for the first wire 61, and various plastics and metals can be used. A super elastic alloy is preferable. By using a super elastic alloy, it becomes possible to provide the distal end portion of the wire main body with high operatability and kink-resistance without increasing the diameter of the first wire 61.

A super elastic alloy (generally shape memory alloy) here means an alloy which exhibits super elasticity at the temperature at which it is used (body temperature, or around 37° C.). The super elasticity is the property possessed by certain alloys that allows them to return to substantially their original shape after having been deformed (bent, extended, or compressed) to an extent such that normal metals are subjected to a plastic deformation.

The preferable composition of the super elastic alloy is Ti-Ni alloy with 49 to 58 atomic percent of Ni, Cu-Zn alloy with 38.5 to 41.5 weight percent of Zn, Cu-Zn-X alloy (X is at least one of Be, Si, Sn, Al, or Ga), or Ni-Al alloy with 36 to 38 atomic percent of Al. Of these alloys Ti-Ni alloy is most preferable.

A thin metal coating 65 is formed on the exterior surface of the proximal end portion 61b of the first wire 61. When the first wire 61 and the connector 63 are made of different materials; for example, the first wire 61 is formed of a super elastic metal and the connector 63 of a stainless steel, it is difficult to connect them by welding. Therefore, a thin metal coating 65 for facilitating welding of Ni, Ag, Au, Sn or Pd, or an alloy of two or more metals selected from these metals is formed on the external surface of the proximal end portion 61b (portion connected to the connector 63) of the first wire 61.

The first wire 61 and the connector 63 are connected by brazing solder filled between the interior surface of the connector 63 and the exterior surface of the first wire 61. For the brazing solder, Ag-Sn alloy, Sn-Pb alloy, Au-Ni alloy, and Sn-Pb-Ni alloy are preferable.

By thus using a thin metal coating formed on the exterior surface of the distal end portion 61b of the first wire 61, the first wire 61 and the connector 63 can be joined firmly by brazing solder. The strength of the connection is high, and the guide wire has a high safety.

To form the metal coating on the exterior surface of the distal end portion 61b of the first wire 61, vapor deposition of the metal to coat (vacuum deposition, for example), ion plating, sputtering, CVD (plasma CVD, electrolytic plating, hydrolysis, pyrolysis, etc.), and dipping can be used. Especially, vapor deposition (vacuum deposition, for example), ion plating, sputtering, plasma CVD, and electrolytic plating, which can be carried out at temperatures which do not affect the property of the super elastic metal used (specifically, methods which can be carried out below about 400° C.). The thickness of the metal coating 65 is preferably about 1 to 10 $\mu$m.

The first wire 61 becomes gradually smaller in exterior diameter toward the distal end, and becomes more flexible toward the distal end. An X-ray contrast material 66 is attached to the distal end portion 61a of the first wire 61. For the X-ray contrast material 66, a coil of wire of an X-ray opaque material such as Platinum wire, for example, is preferable.

A synthetic resin coating 67 is formed on the exterior surface of the first wire 61 excluding the distal end portion, or at least from the middle to the distal end of the first wire 61. This portion has about an uniform exterior diameter. The tip 67a of the synthetic resin coating is rounded approximately in a half sphere.

For the polymer material used for the synthetic resin to cover the first wire 61, polyethylene, poly(vinyl chloride), polyester, polypropylene, polyamide, polyurethane, silicone rubber or other various elastomers, or a composite of these materials is preferable. Especially, materials that have flexibility and softness equal to or greater than those of the first wire 61 are preferable.

Further, it is preferable that the exterior surface of the synthetic resin coating is covered with a hydrophilic macromolecule substance which exhibits lubricity in wet condition. For the method of forming the hydrophilic coating, so called chemical deposition is preferable. By thus covering the exterior surface of the synthetic resin coating with a hydrophilic macromolecule substance, the friction when inserting the guide wire 51 is reduced, and insertion becomes easier. As the result, the operatability of the guide wire increases.

Hydrophilic macromolecule substances usable for this purpose are divided into natural macromolecule substances (starch, cellulose, tannin-lignin, polysaccharide, protein, for example) and synthesized macromolecule substances (PVA, polyethylene oxide, acrylic acid, maleic anhydride, phthalic acid, water-soluble polyester, ketone aldehyde, (meth) acrylamide, polyamine, polyelectrolyte, water-soluble nylon, acrylic acid glycidyl acrylate).

Of the above substances, celluosic macromolecule (hydroxypropyl cellulose, for example), polyethylene oxide macromolecule (polyethylene glycol), maleic anhydride macromolecule (maleic anhydride copolymer such as methyl vinyl ether-maleic anhydride copolymer), acrylamide macromolecule (poly(dimethylacrylamide), for example), water-soluble nylon (AQ-nylon P-70 produced by Toray Industries Inc., for example), or their derivatives are preferable because of their reliability in reducing the coefficient of friction in blood. Reduction of the coefficient of friction by a layer of a hydrophilic macromolecule substance is described in detail in the specification of Patent Application Laid open No. 1997-84871.

The second wire 62 is also a wire with flexibility. There is no special condition for the material for the second wire 62. Various plastics and metals which have higher rigidity than the first wire 61, especially metals, are used. By using these materials, it becomes possible to provide the wire main body with the high operatability and kink-resistance without increasing the diameter of the second wire 62.

The second wire 62 has a larger exterior diameter than the first wire 61 in order to increase the operatability and kink-resistance as shown in FIG. 9. When using the second wire 62 with the external diameter larger than that of the first wire 61, it is preferable to make the external diameter of the distal end portion of the second wire 62 inserted in the connector 63 equal to the external diameter of the proximal portion of the first wire 61 inserted in the connector 63.

The metallic material used for the second wire 62 includes stainless steel or piano wire, for example. The most preferable metallic material is stainless steel which has a high rigidity. Specifically, it is preferable to form the first wire 61 of an super elastic alloy and the second wire 62 of stainless steel. By this construction, a guide wire which has the distal end portion with high flexibility and the proximal end portion with high rigidity and has a gradually changing rigidity can be obtained.

It is preferable that the second wire 62 is subjected to a treatment for reducing the friction which occurs from contact with the interior wall of the catheter used together with the guide wire 51. Specifically, this is attained by coating the proximal portion 62b of the second wire 62 which comes in contact with the interior wall of the catheter, with a substance whose coefficient of friction is low against the material of the interior wall of the catheter (fluororesin such as polytetrafluoroethylene or silicone, for example). By thus reducing the friction against the catheter, the operatability of the second wire 62 passed through the catheter is improved.

The tubular connector 63 has flexibility and is formed in the shape of a tube which has the opening to receive the first wire 61 and the second opening to receive the second wire 62; both openings connect with each other. By using the connector 63 in the shape of a tube, connection of the first wire 61 and the second wire 62 is made easier. Further, the flexural rigidity is made uniform in all radial directions.

There is no special condition for the material for the connector 63, and various plastics and metals can be used as for the first wire 61 and the second wire 62. Especially, the connector 63 is formed of a material different from that of the first wire 61, taking the use of the guide wire into consideration. Further, it is preferable to form the connector 63 of the same or the same kind of material as that of the second wire 62 for connectability to the second wire 62. As the result, stainless steel is preferable for the material of the connector 63.

Although there is no particular limitation to the diameters of the first wire 61, connector 63, and second wire 62, the diameters (in average value) are preferably about 0.25 to 0.65 mm (0.010 to 0.025 inches), and more preferably about 0.36 to 0.45 mm (0.014 to 0.018 inches) for a guide wire used for insertion of a catheter for PTCA operation. A space to fill with a brazing solder is formed between the exterior surface of the first wire 61 and the interior surface of the connector 63. To form this space, the exterior diameter of the first wire 61 is made smaller by about 0.01 to 0.07 mm than the interior diameter of the connector 63. This space can also be made by forming the cross section of the proximal end portion 61b of the first wire 61 in an ellipse, polygon, or other shapes.

The wall thickness of the tubular connector 63 is preferably 0.02 to 0.06 mm, and more preferably 0.03 to 0.05 mm.

The proximal end surface of the first wire 61 and the distal end surface of the second wire 62 are cut at a predetermined angle ($\theta$) to a plane perpendicular to the axes of the first and second wires 61 and 62 as shown in FIGS. 9 and 10. It is preferable to connect the first wire 61 and the second wire 62 holding the end surfaces of the first wire 61 and the second wire 62 in contact with each other inside the connector 63. The angle $\theta$ is $\theta \leq 90°$, preferably $0° < \theta \leq 45°$, and more preferably $0.5° \leq \theta \leq 20°$. The reason is that the change in the rigidity at the end surfaces of the first wire 61 and the second wire 62 in contact with each other can be decreased, and hence a high kink resistance is obtained.

Figure 14:
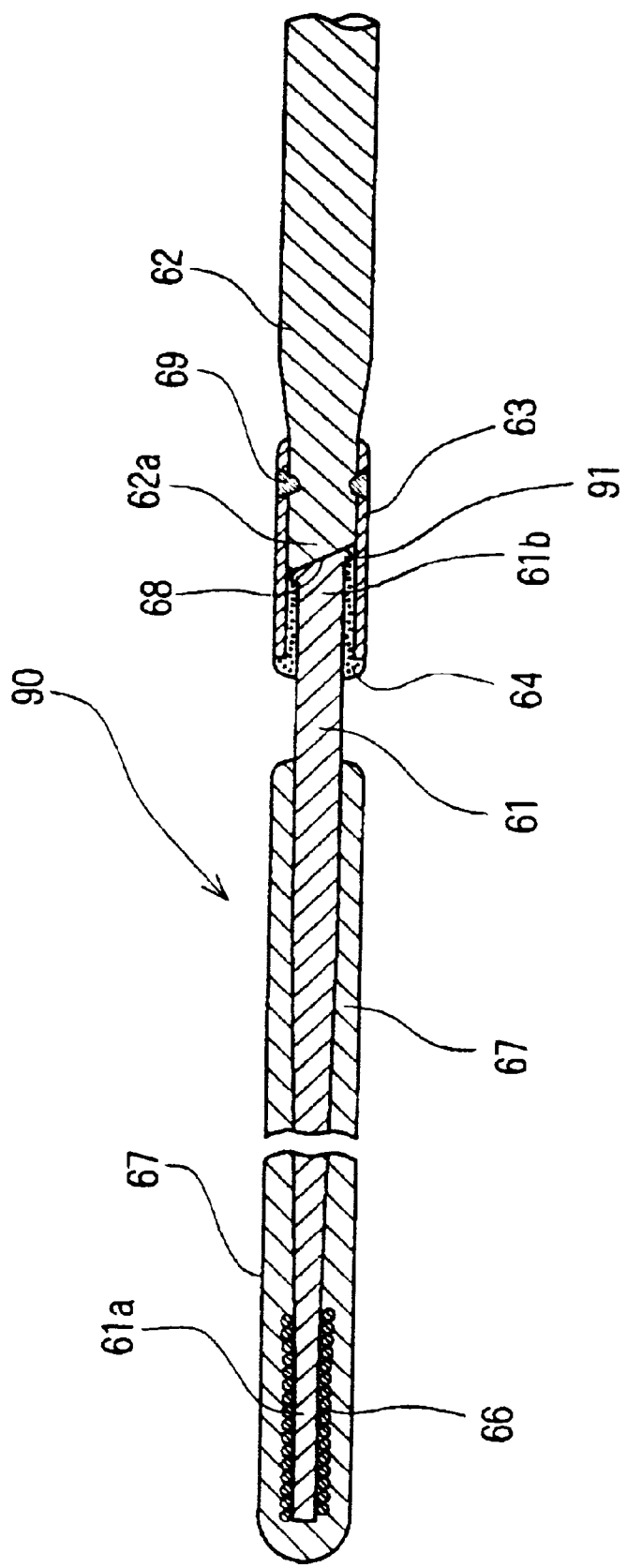
FIG. 14 is a sectional view of the distal end portion of another embodiment of the guide wire of this invention.
Figure 15:
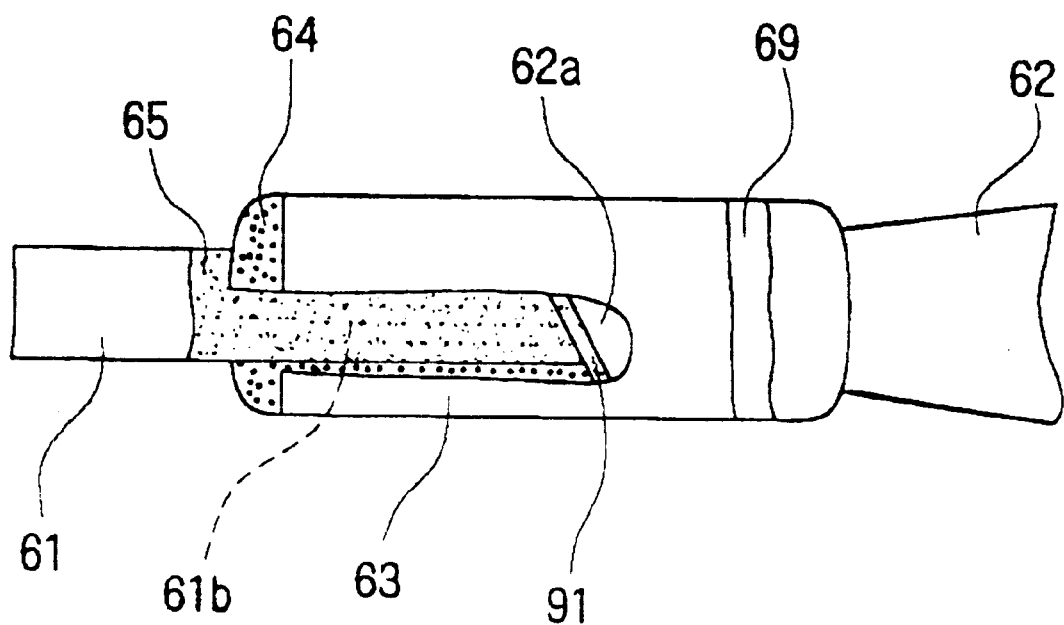
FIG. 15 is a partly-broken, enlarged external view of the connector and its vicinity of the guide wire shown in FIG. 14.

To increase the strength of connection between the first wire 61 and the connector 63, grooves may be formed in the exterior surface of the first wire 61 or in the interior surface of the second wire 62. For the grooves, various shapes and arrangements, such as grooves extending in parallel with the axis of the wires, one or more helical grooves, or grooves perpendicular to the direction of the axis of the wires can be used. Further, to increase the strength of connection by brazing solder 64, a rib may be formed at the proximal end of the first wire 61 as in the guide wire 90 shown in FIGS. 14 and 15. FIG. 14 is a sectional view of the distal end portion of the guide wire of another embodiment of this invention. FIG. 15 is a partly broken, enlarged external view of the connector and its vicinity of the guide wire shown in FIG. 14. For the rib(s) for this purpose, it is preferable to form a rib in the shape of a ring and oblique to the axis of the first wire 61 as shown in FIG. 14 at the proximal end of the first wire 61. Rib(s) in other shapes and arrangements, such as a ring-shaped rib or ribs perpendicular to the axis of the first wire 61 and a plurality of ribs in the shape of a half sphere scattered on the exterior surface of the proximal end portion of the first wire 61.

There is no particular condition for the method of connecting the connector 63 and the second wire 62. In this embodiment, the connector 63 and the second wire 62 are connected by welding to each other. For welding, welding by laser light can be used, for example.

There is also no particular condition for the welded portion 69, as long as they are on the proximal side of the boundary 68. Spot welding at several points are adequate, but it is preferable to dispose the points evenly around the axis in a ring as shown in FIG. 10. The welded portion 69 may have an appropriate width as shown in FIG. 10. It is also possible to weld the entire interior surface of the portion of the connector 63 which is in contact with the exterior surface of the second wire 62. Further, it is also possible to weld the proximal side end of the connector 63.

When forming the connector 63 of a stainless steel with a high rigidity, the wall thickness of the connector 63 can be made thinner. By forming both the second wire 62 and the connector 63 of a stainless steel with a high rigidity, a good weldability can be obtained because of the sameness or similarity of their compositions.

Figure 12:
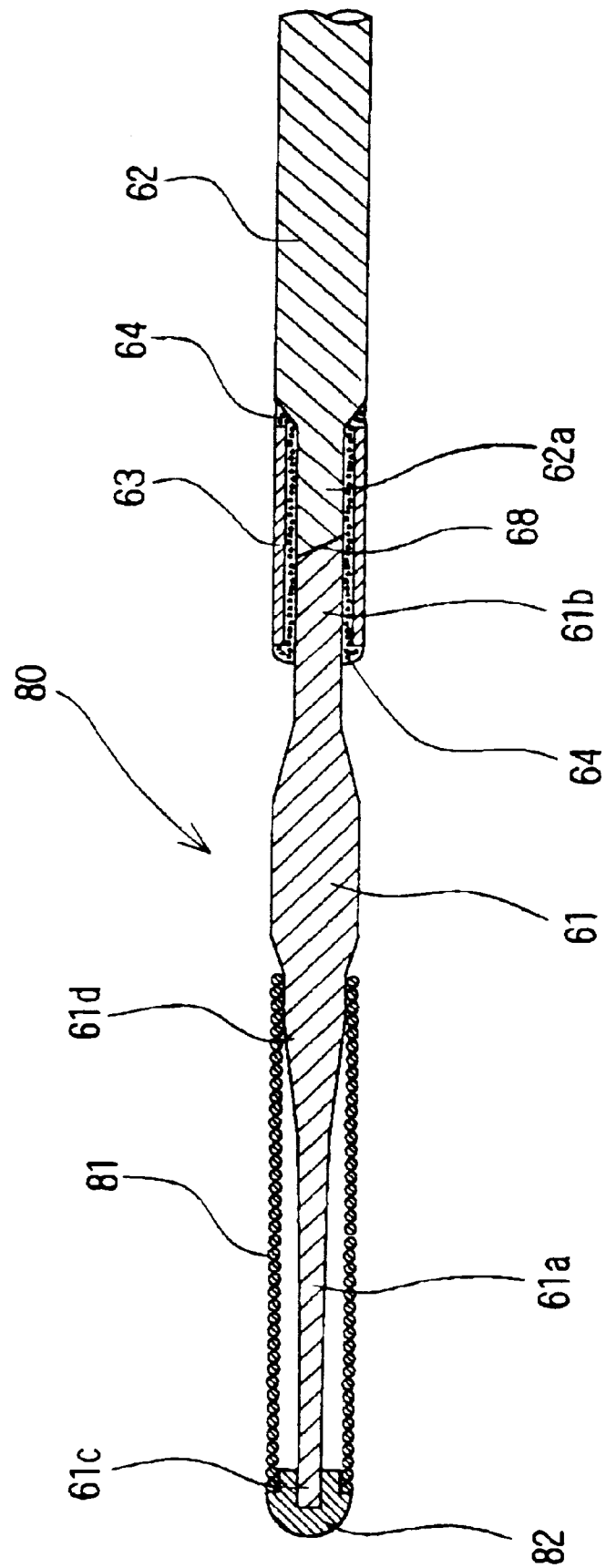
FIG. 12 is a sectional view of the distal end portion of another embodiment of the guide wire of this invention.
Figure 13:
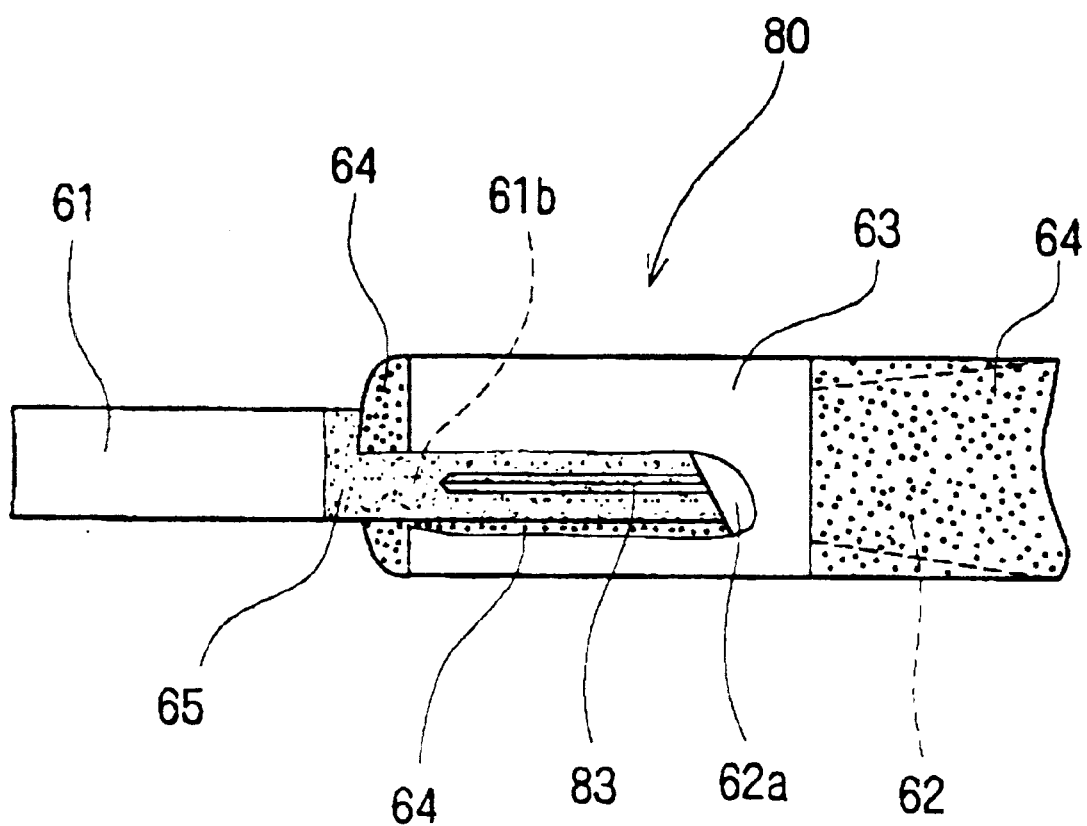
FIG. 13 is a partly-broken, enlarged external view of the connector and its vicinity of the guide wire shown in FIG. 12.

Next, the guide wire 80 of the embodiment shown in FIGS. 12 and 13 is described below.

FIG. 12 is a plan view of the guide wire 80 of another embodiment of this invention. FIG. 13 is a partly-broken, enlarged external appearance of the connector and its vicinity of the guide wire 80 shown in FIG. 12.

The basic construction of this guide wire 80 is the same as the guide wire 51 described above. The same components are assigned the same reference numbers, and the description of them are not repeated.

In this guide wire 80, the connection of the second wire 62 and the connector 63 is also made by brazing 64. For this connection, a space to fill with a brazing solder is formed between the exterior surface of the second wire 62 and the interior surface of the connector 63. To form this space, the exterior diameter of the second wire 62 is made smaller by about 0.01 to 0.07 mm than the interior diameter of the connector 63. Therefore, the distal end portion 62a of the second wire 62 and the proximal end portion 61b of the first wire 61 are made to have about the same exterior diameter. When forming the second wire 62 of the different material from that of the connector 63, a thin metal coating may be formed on the distal end portion 62a of the second wire 62 as on the proximal end portion 61b of the first wire 61 described above.

Further, to increase the strength of connection, grooves may be formed in the exterior surface of the first wire 61 or the interior surface of the connector 63. In the guide wire shown in FIG. 12, V-shaped grooves 83 extending in the direction of the axis are formed in the exterior surface of the first wire 61. Grooves of various shapes and arrangements, such as grooves extending in parallel with the axis, one or more helical grooves, and one or more grooves in the shape of a ring may be used. Grooves may also be formed in the distal end portion 62a of the second wire 62 in the same manner.

A coil 81 wound in the same exterior diameter as the largest-exterior diameter portion of the first wire 61 is attached to the distal end portion of the first wire 61 by being secured by means of the head peace 82 in the shape of a half sphere. The coil 81 and the head peace 82 are formed by an X-ray opaque material such as Au or Pt. The proximal end of the coil 81 is fixed to the first wire 61. The interior diameter of the coil 81 is larger than the exterior diameter of the first wire 61, and a space is formed between the first wire 61 and the coil 81 except the proximal end portion of the coil 81. The coil 81 and the first wire 61 may be secured together at the middle position of the coil 81. Further, the exterior surface of the coil 81 may be covered with a thin synthetic resin coating. For this synthetic resin coating, the same synthetic resins as used for the above-described guide wires can be used. Further, it is preferable to cover the synthetic coating with an above-described hydrophilic macromolecule substance.

It is also possible to form thin metal coating on the distal end 61c of the first wire 61 to which the head peace 82 is attached and on the distal-side tapered portion 61d of the first wire 61, and to connect the head peace 82 and the proximal end of the coil 81 thereto by brazing.

Further, in the above guide wire 51, the construction of the distal end portion of the guide wire (the exterior construction of the first wire 61) may be the same as that of the above guide wire 80.

Next, the guide wire 100 shown in FIGS. 16 to 19 is described below.

Figure 16:
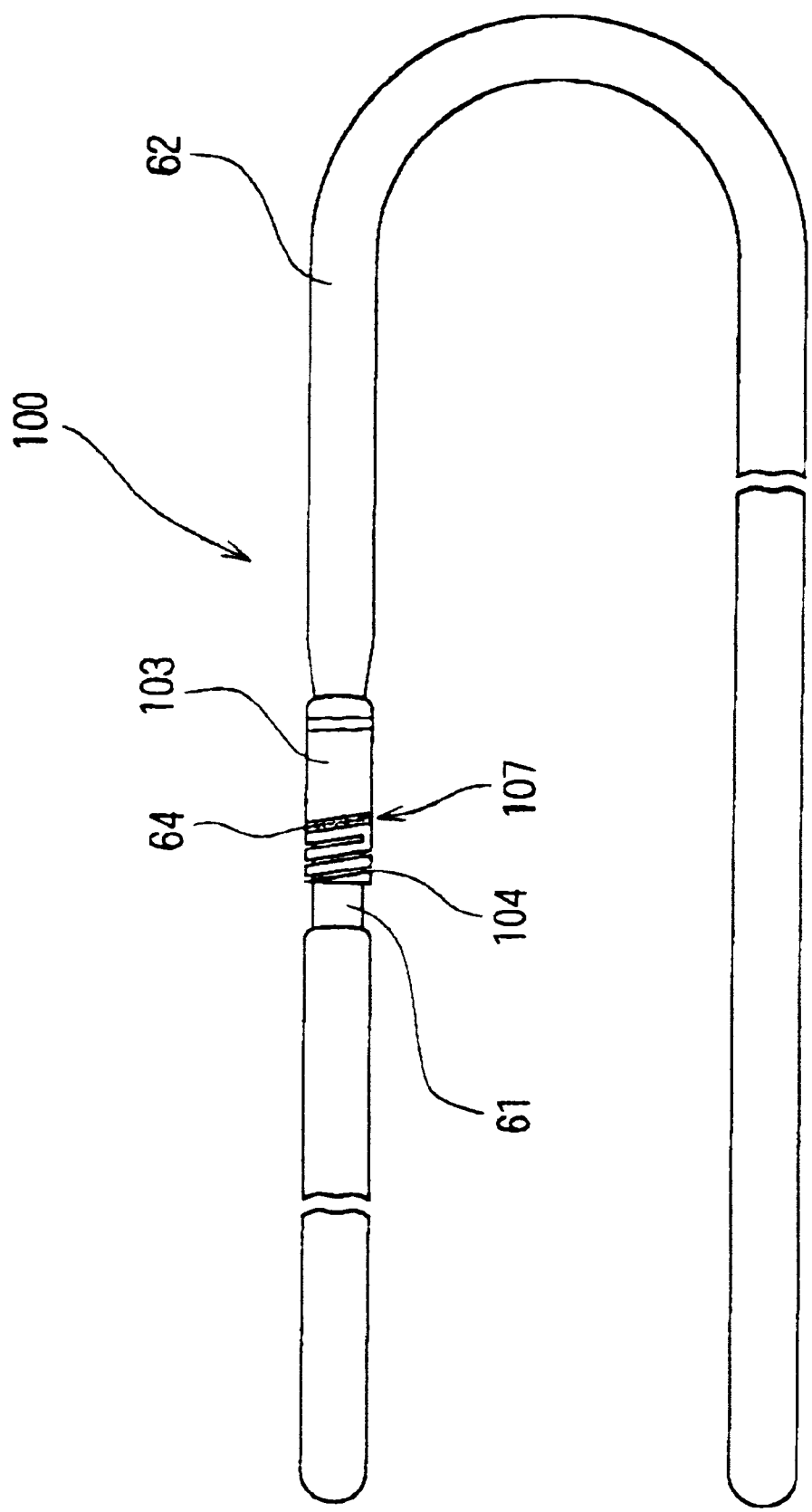
FIG. 16 is a plan view of another embodiment of the guide wire of this invention.
Figure 17:
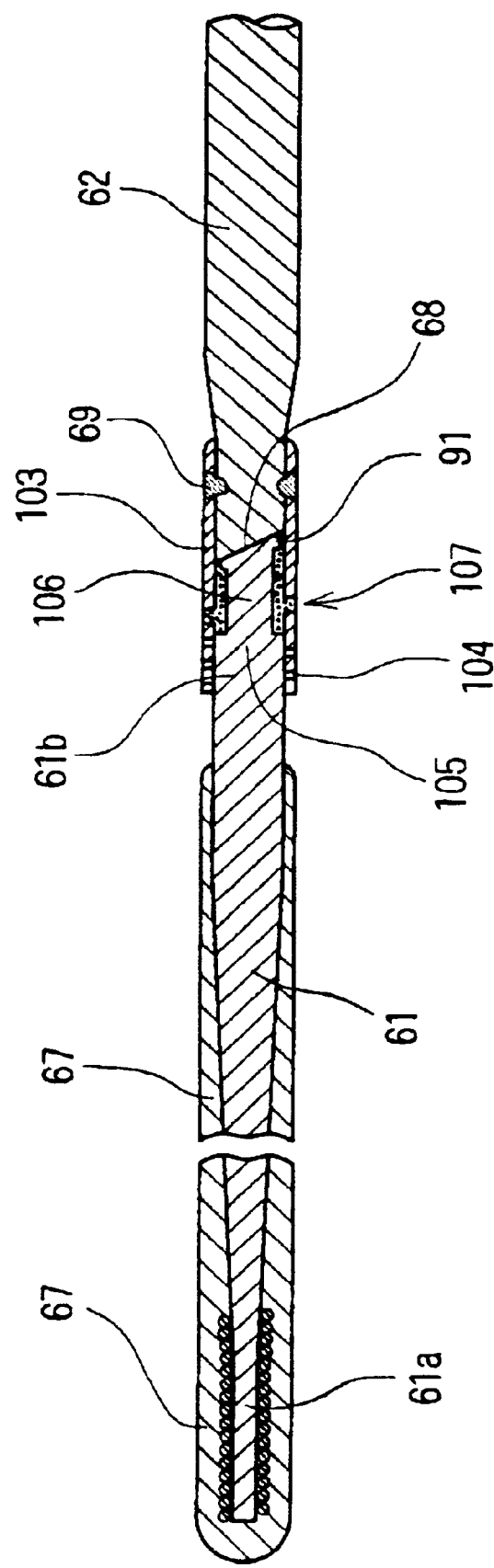
FIG. 17 is a sectional view of the distal end portion of the guide wire shown in FIG. 16.
Figure 18:
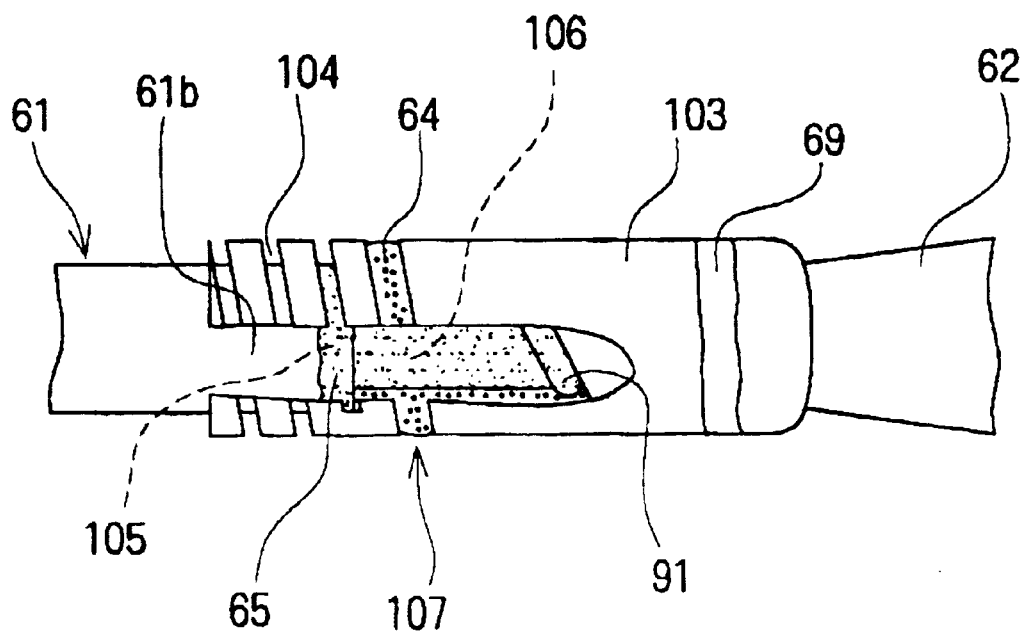
FIG. 18 is a partly-broken, enlarged external view of the connector and its vicinity of the guide wire shown in FIG. 16.
Figure 19:
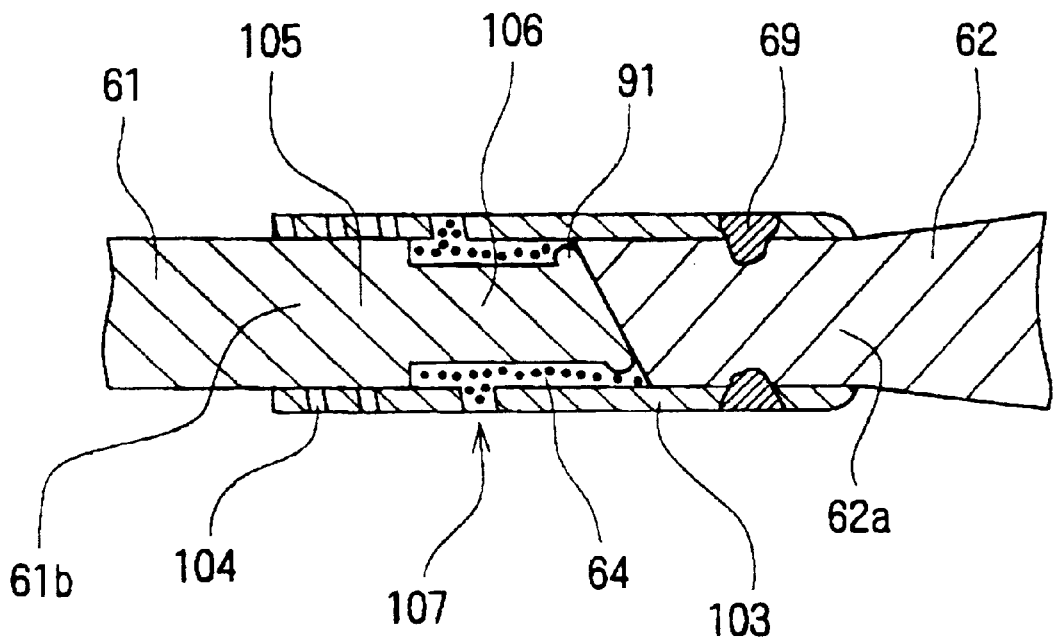
FIG. 19 is an enlarged sectional view of the connector and its vicinity of the guide wire shown in FIG. 16.

FIG. 16 is a plane view of the guide wire 100 of this invention. FIG. 17 is a sectional view of the distal end portion of the guide wire shown in FIG. 16. FIG. 18 is a partly broken, enlarged external view of the connector and its vicinity of the guide wire shown in FIG. 16. FIG. 19 an enlarged sectional view of the connector and its vicinity of the guide wire shown in FIG. 16.

The basic construction of this guide wire 100 is the same as the guide wire 51 described above. The same components are assigned the same reference numbers, and the description of them are not repeated. The points in which the guide wire 100 differs from the above guide wire 51 are only the shape of the connector 103 and the method of connection of the first wire 61 and the connector 103.

The guide wire 100 for catheter of this embodiment comprises the first wire 61 which is disposed at the distal side and has flexibility, the second wire 62 which is disposed at the proximal side and has rigidity greater than that of the first wire 61, and a tubular connector 103 for connecting the first wire 61 and the second wire 62 which is formed of a material different from that of the first wire 61. The first wire 61 has a thin metal coating 65 for connection to the connector 103 formed on its proximal end portion connected to the connector 103. The first wire 61 and the connector 103 are joined together by brazing solder 64 by making use of the thin metal coating.

A thin metal coating 65 is formed on the exterior surface of the distal end portion 61b of the first wire 61 as in the above guide wire 51. For the material for the thin metal coating 65, Ni, Ag, Au, Cu or Sn, or an alloy of two or more metals selected among them is used.

The connector 103 has the opening to receive the first wire 61 and the second opening to receive the second wire 62; both openings connect with each other, the entire connector 103 being in the shape of a tube.

The connector 103 has a first slit 104 in the distal end portion. Specifically, the first slit 104 extends from the distal end to the middle part of the connector 103. This first slit 104 is a helical slit.

In the guide wire 100, the second wire 62 is made of a metal whose rigidity is greater than that of the first wire 61 and the connector 103 is made of the same or same kind of material as the second wire 62. The connector 103 has a slit, therefor the rigidity of the guide wire 100 provided the connector 103 is made to increase smoothly from a proximal end portion of the first wire 61 to a distal end portion of the second wire 62.

The connector 103 has a second slit 107, a separate slit from the slit 104, is formed on the proximal side of the first slit 104, that is, near the middle part of the connector 103. This slit 107 is also a helical slit. The second slit 107 has a wider width than the first slit 104 and serves as the opening for pouring brazing solder 64. Instead of a helical slit, the second slit 107 may be a plurality of separate short slits. It is preferable that this second slit 107 does not extend toward the proximal side beyond the boundary 68.

The first wire 61 has the first proximal end portion 105 of approximately the same exterior diameter as the interior diameter of the connector 103 and the second proximal end portion 106 which further extends from the first proximal end portion 105 to the proximal side and form a space to fill with brazing solder between its exterior surface and the interior surface of the connector 103. In this example, the second proximal end portion 106 has an external diameter smaller than the interior diameter of the connector 103. The space to fill with brazing solder may also be formed by forming the cross section of the second proximal end portion 106 in ellipse, polygon, or other shapes.

The second slit 107 serving as the opening for pouring brazing solder 64 is located above the space to be filled with brazing solder and communicates the space with the outside. A rib 91 is formed at the proximal end of the first wire 61. To increase the strength of connection, one or more grooves may be formed in the exterior surface of the second proximal end portion 106 of the first wire 61 or in the interior surface of the portion of the connector 103 which forms the space to be filled with brazing solder. For the grooves, various shapes and arrangements, such as grooves extending in parallel with the axis of the wires, one or more helical grooves, or grooves perpendicular, may be used.

Further, the distance between the adjacent slits, or the pitch of the first slit 104, may be changed to change the rigidity. Specifically, the pitch of the slit 104 is made so as to become smaller toward the distal end of the connector 103. The width of the slit 104 becomes larger toward the distal end of the connector 103. By thus forming the first slit 104, the rigidity of the connector 103 becomes gradually smaller toward the distal end, the deformation of the distal end portion of the guide wire becomes smoother. It is also possible to form two or more helical slits instead of a single slit. Further, two or more slits in parallel with the axis maybe formed in place of the helical first slit 104. When forming two or more slits in parallel with the axis, it is preferable to make the width of the slots wider at their proximal end. Further, the first slit 104 and the second slit 107 may be connected to each other.

When forming the first slit 104 and the second slit 107 in a single continuous slit, it is preferable to make wider the width of the second slit 107 than that of the first slit 104.

Brazing solder is poured through the second slit 107 into the space formed between the connector 103 and the second distal end portion 106, as shown in FIGS. 18 and 19. The brazing solder fills the space and the second slit 107. Thus the first wire 61 is firmly connected to the connector 103. The brazing solder 64 does not fill the first slit 104, and the space formed by the first slit 104 is left unfilled. The portion of the connector 103 in which the first slit is formed is not connected to the first wire 61.

The guide wire of this embodiment has a flexible portion at the distal side of the connector 103 which is formed by the first slit 104 formed therein. Therefore, kinking of the guide wire at the distal end of the connector 103 can be prevented. Moreover, the guide wire can bend at the distal end of the connector 103. Moreover, since the guide wire can bend at the distal end of the connector 103, the operatability of the guide wire is improved. Also, because the distal end portion of the connector 103 in which the first slit is formed is not connected to the first wire 61, the guide wire of this embodiment has high kink resistance and operatability.

As understood by the above description, this invention makes it possible to connect the first wire and the connector formed of different materials together with an adequate strength, changing the rigidity gradually and smoothly from the rigidity of the first wire to that of the second wire. Especially, by forming a thin metal coating on the exterior surface of the proximal end portion of the first wire which is held in the connector, the first wire and the connector can be firmly connected by brazing if the first wire and the connector are made of different materials. Therefore, the guide wire of this invention has an improved operatability and a high safety.

What is claim is:

1. A guide wire, comprising a first wire which is located on a distal end of the guide wire, a second wire which is located on a proximal end of the guide wire and has a flexural rigidity greater than that of said first wire, and a tubular connector joining said first and second wires, said connector having a groove or a slit or both formed in its portion on a distal side of a boundary between said first wire and said second wire, the flexural rigidity of a portion of the connector on the distal side of the boundary between said first wire and said second wire changes smoothly along its length.

2. The guide wire of claim 1 wherein a flexural rigidity of a proximal end portion of said first wire joined to said connector changes smoothly along its length.

3. The guide wire of claim 1 wherein a pitch or interval of said groove or slit formed in said tubular connector becomes larger toward a distal end of said tubular connector.

4. The guide wire of claim 1 wherein said second wire is formed of a metal, and said connector is formed of the same or the same kind of material as said second wire.

5. The guide wire of claim 4 wherein said first wire is formed of a super elastic metal and said second wire is made of a stainless steel.

6. The guide wire of claim 1 wherein said first wire and said connector, and said second wire and said connector are joined by welding.

7. The guide wire of claim 1 wherein the first and second wires include abutting end surfaces that abut one another, the first and second wires also including respective central axes, the abutting end surfaces of said first and second wires being oblique to a plane perpendicular to the central axes of said first and second wires.

8. The guide wire of claim 1 wherein said second wire is made of a metal whose rigidity is greater than that of the first wire and said connector is made of the same or same kind of material as said second wire, and the rigidity of the guide wire increases smoothly from a proximal end portion of said first wire toward a distal end portion of said second wire.

9. A guide wire comprising a first wire which is located on a distal end of the guide wire, a second wire which is located on a proximal end of the guide wire and has a flexural rigidity greater than that of said first wire, and a tubular connector for joining said first and second wires, said connector being formed of a material different from a material of said first wire, a proximal portion of said first wire joined to said connector being provided with a thin metal coating as an adjuvant to joining, said first wire being joined to said connector by brazing, and a helical slit formed in a proximal end portion of the connector.

10. The guide wire of claim 9 wherein said first wire is formed of a super elastic metal and said thin metal coating is formed of Ni, Ag, Au, Sn or Pd, or an alloy of two or more of these metals.

11. The guide wire of claim 9 wherein said connector is formed of a stainless steel.

12. The guide wire of claim 9 wherein said connector and said second wire are formed of a stainless steel and joined by welding.

13. The guide wire of claim 9 wherein the first and second wires have abutting end surfaces that abut one another, the first and second wires having respective central axes, the abutting end surfaces of said first and second wires being oblique to a plane perpendicular to the central axes of said first and second wires.

14. The guide wire of claim 9 wherein at least a distal end portion of said portion of said connector where said slit is formed is not joined to said first wire.

15. The guide wire of claim 9 wherein a flexural rigidity of a portion of the connector on a distal side of a boundary between said first wire and said second wire changes smoothly along its length.

16. The guide wire of claim 9 wherein said second wire is made of a metal whose rigidity is greater than that of the first wire and said connector is made of the same or same kind of material as said second wire, and the rigidity of the guide wire increases smoothly from a proximal end portion of said first wire to a distal end portion of said second wire.

17. A guide wire, comprising a first wire located on a distal end of the guide wire, a second wire located on a proximal end of the guide wire and having a flexural rigidity greater than that of said first wire, and a tubular connector joining said first and second wires, said connector having a groove, a slit or both a groove and a slit formed in its portion located on a distal side of a boundary between said first wire and said second wire, said second wire being made of a metal whose rigidity is greater than that of the first wire and said connector being made of the same or same kind of material as said second wire, the rigidity of the guide wire increasing smoothly from a proximal end portion of said first wire to a distal end portion of said second wire.

18. The guide wire of claim 17 wherein a flexural rigidity of a portion of connector on a distal side of the boundary between said first wire and said second wire changes smoothly along its length.

19. The guide wire of claim 17 wherein a pitch or interval of said groove or slit formed in said tubular connector becomes larger toward a distal end of said tubular connector.

20. The guide wire of claim 17 wherein the first wire is formed of a super elastic metal and said second wire is made of a stainless steel.

21. The guide wire of claim 17 wherein said first wire and said connector are joined by welding, and said second wire and said connector are joined by welding.

22. The guide wire of claim 17 wherein the first and second wires have abutting end surfaces that abut one another, the first and second wires having respective central axes, the abutting end surfaces of said first and second wires being oblique to a plane perpendicular to the central axes of said first and second wires.

* * * * *

UNITED STATES PATENT AND TRADEMARK OFFICE
CERTIFICATE OF CORRECTION

PATENT NO. : 6,001,068  
DATED : December 14, 1999  
INVENTOR(S) : Syunichi Uchino et al.

Page 1 of 1

It is certified that error appears in the above-identified patent and that said Letters Patent is hereby corrected as shown below:

Title page,
Item [57],
Line 1, after "wire." and before "The" insert
-- According to another aspect of the invention, a guide wire includes a first wire located at the distal end of the guide wire, a second wire located at the proximal end of the guide wire and having a flexural rigidity greater than that of the first wire, and a tubular connector for joining the first and second wires. --

Signed and Sealed this

Eleventh Day of December, 2001

Attest:

NICHOLAS P. GODICI
*Attesting Officer*     *Acting Director of the United States Patent and Trademark Office*